(12) United States Patent
Murty et al.

(10) Patent No.: US 9,265,724 B2
(45) Date of Patent: Feb. 23, 2016

(54) ORAL DOSAGE FORM OF TETRAHYDROCANNABINOL AND A METHOD OF AVOIDING AND/OR SUPPRESSING HEPATIC FIRST PASS METABOLISM VIA TARGETED CHYLOMICRON/LIPOPROTEIN DELIVERY

(76) Inventors: Ram B. Murty, Lexington, KY (US); Santos B. Murty, Lexington, KY (US)

(*) Notice: Subject to any disclaimer, the term of this patent is extended or adjusted under 35 U.S.C. 154(b) by 405 days.

(21) Appl. No.: 12/876,292

(22) Filed: Sep. 7, 2010

(65) Prior Publication Data

US 2011/0092583 A1 Apr. 21, 2011

Related U.S. Application Data

(63) Continuation-in-part of application No. 11/592,393, filed on Nov. 3, 2006, now abandoned.

(60) Provisional application No. 60/734,160, filed on Nov. 7, 2005.

(51) Int. Cl.

| | | |
|---|---|---|
| A61K 31/352 | (2006.01) | |
| A61P 1/08 | (2006.01) | |
| A61P 25/06 | (2006.01) | |
| A61P 27/06 | (2006.01) | |
| A61P 25/22 | (2006.01) | |
| A61P 25/30 | (2006.01) | |
| A61K 9/107 | (2006.01) | |
| A61K 9/48 | (2006.01) | |
| A61K 31/353 | (2006.01) | |
| A61K 31/655 | (2006.01) | |
| A61K 47/10 | (2006.01) | |
| A61K 47/12 | (2006.01) | |
| A61K 47/14 | (2006.01) | |
| A61K 47/22 | (2006.01) | |
| A61K 47/44 | (2006.01) | |

(52) U.S. Cl.
CPC .............. *A61K 9/107* (2013.01); *A61K 9/4858* (2013.01); *A61K 31/353* (2013.01); *A61K 31/655* (2013.01); *A61K 47/10* (2013.01); *A61K 47/12* (2013.01); *A61K 47/14* (2013.01); *A61K 47/22* (2013.01); *A61K 47/44* (2013.01)

(58) Field of Classification Search
CPC ....................................................... A61K 6/00
See application file for complete search history.

(56) References Cited

U.S. PATENT DOCUMENTS

| | | | | |
|---|---|---|---|---|
| 6,566,560 | B2 * | 5/2003 | Travis | 568/715 |
| 6,730,330 | B2 * | 5/2004 | Whittle et al. | 424/725 |
| 2002/0136752 | A1 | 9/2002 | Whittle et al. | |
| 2006/0160888 | A1 * | 7/2006 | Kottayil et al. | 514/454 |
| 2007/0298099 | A1 * | 12/2007 | Peresypkin et al. | 424/456 |

FOREIGN PATENT DOCUMENTS

| | | |
|---|---|---|
| WO | 94/05298 A1 | 3/1994 |
| WO | 95/25505 A1 | 9/1995 |
| WO | 95/27479 A1 | 10/1995 |

OTHER PUBLICATIONS

Thomas et al. Cannabidiol Dislplays Unexpectedly High Potency as an Antagonist of CB1 and CB2 Receptor Agonists In Vitro. British Journal of Pharmacology (2007) pp. 613-623.*
International Search Report and Written Opinion issued on Jan. 3, 2011, in PCT Application No. PCT/US2010/047952, filed on Sep. 7, 2010.

\* cited by examiner

*Primary Examiner* — Scott Long
*Assistant Examiner* — Sarah Alawadi
(74) *Attorney, Agent, or Firm* — King & Schickli, PLLC

(57) ABSTRACT

Self-emulsifying drug delivery systems are provided to improve dissolution, stability, and bioavailability of drug compounds of dronabinol or other cannabinoids. The drug compound(s) are dissolved in an oily medium (e.g. triglycerides and/or mixed glycerides and/or free fatty acids containing medium and/or long chain saturated, mono-unsaturated, and/or poly-unsaturated free fatty acids) together with at least one surfactant. The surfactant promotes self-emulsification, thereby promoting targeted chylomicron/lipoprotein delivery and optimal bioavailability through the mammalian intestinal tract. A dosage form can optionally include co-solvents, antioxidants, viscosity modifying agents, cytochrome P450 metabolic inhibitors, P-GP efflux inhibitors, and amphiphilic/non-amphiphilic solutes to induce semi-solid formation for targeted release rates.

11 Claims, 3 Drawing Sheets

ORAL DOSAGE FORM OF TETRAHYDROCANNABINOL AND A METHOD OF AVOIDING AND/OR SUPPRESSING HEPATIC FIRST PASS METABOLISM VIA TARGETED CHYLOMICRON/LIPOPROTEIN DELIVERY

REFERENCE TO RELATED APPLICATIONS

This continuation-in-part application claims the benefit of U.S. provisional application No. 60/734,160, filed on Nov. 7, 2005, and U.S. application Ser. No. 11/592,393, filed Nov. 3, 2006, now abandoned, the contents of both of which are incorporated herein by reference.

FIELD OF THE INVENTION

The present invention relates in general to a delivery system to improve administration of cannabinoids to patients and, more particularly, through a self-emulsifying drug delivery system. The drug delivery system of the present invention optimizes cannabinoid dissolution properties and avoids hepatic first-pass metabolism, thereby enhancing bioavailability through the gastrointestinal tract. The delivery system of the present invention can be administered as either a liquid or semi-solid matrix within a capsule shell for immediate or sustained release rates.

BACKGROUND OF THE INVENTION

Cannabinoids are compounds derived from the cannabis sativa plant commonly known as marijuana. The plant contains more than 400 chemicals and approximately 60 cannabinoids. The most active chemical compound of the naturally occurring cannabinoids is tetrahydrocannabinol (THC), particularly $\Delta^9$-THC.

Currently, $\Delta^9$-tetrahydrocannabinol, also known as dronabinol, is available commercially in Marinol® soft gelatin capsules which have been approved by the Food and Drug Administration (FDA) for the control of nausea and vomiting associated with chemotherapy and for appetite stimulation of AIDS patients suffering from the wasting syndrome. $\Delta^9$-tetrahydrocannabinol shows other biological activities, which lend themselves to possible therapeutic applications, such as in the treatment of glaucoma, migraine headaches, spasticity, anxiety, analgesia, and drug addiction.

In Marinol®, $\Delta^9$-THC is dissolved in sesame oil and encapsulated in gelatin capsules for oral administration. After oral administration, Dronabinol has an onset of action of approximately 0.5 to 1 hour, with a peak effect of 2-4 hours. The duration of action for psychoactive effects is 4-6 hours, but the appetite stimulant effect may continue for 24 hours or longer after administration. The maximal plasma levels after oral dosing of 20 mg $\Delta^9$-THC in a sesame oil formulation are around 10 ng/ml.

At the present time, some cancer patients manage to obtain prescriptions for marijuana in order to alleviate pain as well as nausea and vomiting due to chemotherapy. This latter situation arises due to poor or partial response from oral therapy, which often requires oral administration two to three times a day to obtain equivalent acute psychological and physiological effects obtained from smoking marijuana.

When administered orally, $\Delta^9$-THC or dronabinol is almost completely absorbed (90-95%) after a single oral dose. However, due to the combined effect of first pass hepatic metabolism and high lipid solubility, only about 10-20% of an administered dose reaches systemic circulation with highly variable maximal concentrations. It has been found that fasting or food deprivation may decrease the rate of absorption of $\Delta^9$-THC from the sesame oil capsules currently available in the market. Previous studies have reported that another limitation of orally administered $\Delta^9$-THC is the large inter-subject variability in absorption.

Other postulated mechanisms for the biopharmaceutical anomalies can be attributed to the physical-chemical properties of $\Delta^9$-THC. This compound is highly lipophilic, essentially water insoluble, and potentially acid labile within the stomach. This compound is also sensitive to environmental storage and stress conditions. For instance, this compound is thermolabile and photolabile, and long-term storage can lead to a cumulative decrease in $\Delta^9$-THC content by an oxidation reaction forming cannabinol (CBN).

It is well known that in mammals certain areas of the alimentary canal have a venous drainage, which does not involve a first pass through the liver. The avoidance of the first pass effect is the rationale for the use of rectal, buccal, nasal, and sublingual formulations. A $\Delta^9$-THC and cannabidiol combination has been formulated as a buccal spray. Some of the disadvantages associated with nasal, sublingual and buccal routes of administration are that the nasal mucosa may cause pain or reflex sneezing and, in extreme cases, may cause irritation and damage to the nasal mucosa. Sublingual formulations may stimulate the flow of saliva, making it difficult for patients to avoid swallowing when substantial amounts of saliva are produced. Also, buccal formulations may be subject to the same limitations as sublingual formulations.

Both sublingual and buccal formulations depend on the efficient transfer of medicament from a hydrophilic vehicle to the mucous membrane of the sublingual or buccal mucosa. Transfer of medicament through the interstices between or through epithelial cells is governed principally by the lipid solubility of the medicament. When a drug is water insoluble as in the case with cannabinoids, this presents a further barrier to absorption from the sublingual area.

In an effort to improve local drug delivery of $\Delta^9$-THC, researchers have tried to develop a transdermal delivery system. The bioactive material administered dermally, however, may show erratic and irregular absorption. Hence, the need exists for the addition of absorption enhancers which in some cases may be detrimental to the skin due to local side effects.

Other delivery systems for $\Delta^9$-THC or cannabinoids described in the patent literature, include: Metered dose inhaler using non-CFC propellants (U.S. Pat. Nos. 6,509,005 and 6,713,048); Pump action spray (U.S. Pat. No. 6,946,150); Microsphere nasal delivery system (U.S. Pat. No. 6,383,513); Water soluble prodrugs for intranasal administration (U.S. Pat. No. 6,380,175); Topical liniment (U.S. Pat. No. 6,949,582); Cyclodextrin complexes with cannabinoids (U.S. Patent Application No. 20050153931); and solid lipid compositions for oral administration (U.S. Pat. Nos. 5,891,469 and 5,989,583).

This solid lipid composition involves a method for delivering a non-psychoactive cannabinoid (i.e. dexanabinol) in a dry lipid mixture to greatly enhance oral bioavailability when compared to known formulations. With enhanced absorption characteristics of oral delivery systems, the patentees anticipated that treatment could be directed towards brain damage associated with stroke, head trauma, and cardiac arrest. This, however, required sufficient bioavailability of the drug compound. Oral $\Delta^9$-THC or dronabinol therapy would be greatly benefited by improved bioavailability for treating a variety of conditions described above.

Oral dosage forms are designed to enable sufficient availability of the active compound at its site of action. The bioavailability of a drug depends on several parameters, i.e., the physicochemical nature of the active compound, the dosage form, as well as physiological factors. The cannabinoid compounds, being hydrophobic by nature, show wetting difficulties and poor dissolution in the gastrointestinal region. In addition, $\Delta^9$-THC or dronabinol undergo extensive hepatic first-pass metabolism. These properties represent barriers to drug absorption from oral dosage forms. These barriers in turn cause a subsequent reduction in the bioavailability.

To compensate for the poor absorption displayed by many drugs, a pharmaceutical formulation may utilize or take advantage of one or more mechanisms to increase the rate and/or the extent to which the administered drug is absorbed.

Dronabinol or $\Delta^9$-THC belongs to Class II (low aqueous solubility and high permeability) of the biopharmaceutical classification system (BCS). Hence, there may be an advantage associated with a self-emulsifying (SEDDS) lipid based delivery system to enhance the dissolution of a drug system in an aqueous environment. Patents demonstrating the potential use of SEDDS or lipid delivery systems for lipophilic drugs are U.S. Pat. Nos. 5,484,801; 5,798,333; 5,965,160; 6,008,228; 6,730,330. See also U.S. Patent Application No. 20050209345, and International Application No. PCT/EP96/02431 (WO 96/39142)).

There are no known reports disclosing the oral delivery of $\Delta^9$-THC based on SEDDS technology to improve the dissolution characteristics and to increase the oral bioavailability through chylomicron/lipoprotein assembly for subsequent transport through the lymphatic system. $\Delta^9$-THC dosage forms intended for other routes of administration are subjected to high intra and inter patient variability.

However, SEDDS systems have not been used with cannabinoids for a number of reasons; first, due to the possibility that the SEDDS system may undergo gastric emptying while in a colloidal state; second, or the emulsifying system may result in rapid absorption and higher peak concentrations of the drug; third, large concentrations of surfactant in the SEDDS system may cause gastrointestinal irritation.

Therefore, one of the objects of the present invention is to provide a more optimized and improved delivery system for $\Delta^9$-THC to meet the desired needs of the patients.

It is still another object of the present invention to provide an oral dosage form of $\Delta^9$-THC or dronabinol, which provides sufficient bioavailability of this drug for the treatment of numerous medical complications for which the drug can be therapeutically beneficial (e.g. brain damage associated with stroke, heat trauma, and cardiac arrest).

It is another object of the present invention to provide a pharmaceutical formulation which compensates for poor absorption displayed by $\Delta^9$-THC or dronabinol.

It is yet another object of the present invention to provide a pharmaceutical formulation for $\Delta^9$-THC or dronabinol which does not result in gastric emptying while in a colloidal state.

It is another object of the present invention is to provide a pharmaceutical formulation for $\Delta^9$-THC or dronabinol which does not cause gastrointestinal irritation.

Another object of the present invention is to promote drug absorption through alternate gastrointestinal pathways, outside the conventional hepatic portal vein transport mechanism, which results in a high first-pass effect.

SUMMARY OF THE INVENTION

The inventors herein, after extensive investigation and research, unexpectedly discovered an oral dosage form of cannabinoids which achieve the above objectives of the present invention.

The present invention provides an isotropic phased and chemically stabilized oral delivery system of dronabinol or other cannabinoids. The drug compound(s) are dissolved in an oily medium (e.g. triglycerides and/or mixed glycerides and/or medium/long chain saturated, mono-unsaturated, and poly-unsaturated fatty acids) with at least one surfactant to promote self-emulsification. This formulation was unexpectedly found to promote targeted chylomicron/lipoprotein delivery, and optimal bioavailability after administration through the mammalian intestinal tract where endogenous bile salts reside.

The SEDDS formulation of the present invention preferably falls under one of the three categories, Type I, Type II, and Type III, which are defined as isotropic mixtures. These mixtures contain the following types of ingredients: (1) natural or synthetic oily mediums, (2) solid or liquid surfactants, and (3) one or more hydrophilic solvents and co-solvents/surfactants.

Preferably, for $\Delta^9$-THC SEDDS, Types I, II, & III may be categorized as follows:

(i) Type I formulations consist of an oily medium (e.g. triglycerides and/or mixed glycerides and/or medium/long chain saturated, mono-unsaturated, and poly-unsaturated free fatty acids); whereas the oily medium may also be polyfunctional with potential surfactant characteristics to promote self-emulsification. Mixed glycerides are defined herein as glycerols which have been esterified with fatty acids at one or two hydroxyl groups on the glycerol to form mono or diglycerides.

(ii) Type II consist of an oily medium (e.g. triglycerides and/or mixed glycerides and/or medium/long chain saturated, mono-unsaturated, and poly-unsaturated free fatty acids) and at least one surfactant component to promote self-emulsification.

(iii) Type III consist of an oily medium (e.g. triglycerides and/or mixed glycerides and/or medium/long chain saturated, mono-unsaturated, and poly-unsaturated free fatty acids) and at least one surfactant component to promote self-emulsification, and at least one hydrophilic cosolvent.

Optionally, the dosage form can include co-solvents, antioxidants, viscosity modifying agents, cytochrome P450 metabolic inhibitors, P-GP efflux inhibitors, and finally amphiphilic/non-amphiphilic solutes to induce semi-solid formation for targeted release rates.

Upon administration as an isotropic liquid, semi-solid, or waxy solid phase and upon initial dilution in the gastric region of a mammal, the contents immediately form dispersion for protection against acid catalyzed degradation of cannabinoids. With gastric emptying of the dispersion into the intestinal lumen, further solubilization with bile salts and downstream processing promote the selective discriminative transport of drug into lipid absorption pathways, particularly chylomicron/lipoprotein assembly in the endoplasmic reticulum of the intracellular environment of enterocytes, thereby promoting lymphatic transport and thus avoiding hepatic first-pass metabolism.

An isotropic semi-solid or waxy solid phase is prepared by dissolving a high concentration of ascorbyl palmitate (or other amphiphilic/non-amphiphilic solutes) in an oily liquid state as described above. Upon administration as an isotropic semi-solid phase and upon initial dilution in the gastric region of a mammal, the contents immediately form a dispersion for protection against acid catalyzed degradation of cannabinoids.

With gastric emptying of the dispersion into the intestinal lumen, further solubilization with bile salts and downstream processing promote the selective discriminative transport of a drug into lipid absorption pathways, particularly chylomicron/lipoprotein assembly in the endoplasmic reticulum of the intracellular environment of enterocytes, thereby promoting lymphatic transport and thus avoiding hepatic first-pass metabolism.

The self-emulsifying formulations of the present invention for $\Delta^9$-THC may be categorized as follows:

(i) Type I formulations consist of an oily medium (e.g. triglycerides and/or mixed glycerides and/or medium/long chain saturated, mono-unsaturated, and poly-unsaturated free fatty acids); whereas the oily medium may also be polyfunctional with potential surfactant characteristics to promote self-emulsification.

(ii) Type II consists of an oily medium (e.g. triglycerides and/or mixed glycerides and/or medium/long chain saturated, mono-unsaturated, and poly-unsaturated free fatty acids), and at least one surfactant component to promote self-emulsification.

(iii) Type III consist of an oily medium (e.g. triglycerides and/or mixed glycerides and/or medium/long chain saturated, mono-unsaturated, and poly-unsaturated free fatty acids) and at least one surfactant component to promote self-emulsification, and at least one hydrophilic cosolvent.

In a first preferred embodiment there is provided an oral dosage form of cannabinoids in a self-emulsifying system operable to avoid hepatic first pass metabolism via targeted chylomicron/lipoprotein delivery, thereby promoting lymphatic transport, said oral dosage form comprising:

(a) about 1-90 wt % of a pharmacologically active form of cannabinoids;

(b) about 15-85 wt % of one or more triglycerides formed from long chain fatty acids having from $C_{13}$ to $C_{24}$ carbon atoms, with about 5 to 95 wt % of said long chain fatty acids being polyunsaturated, and from about 5 to 95 wt % of said long chain fatty acids being monosaturated;

(c) about 15-85 wt % of one or more mixed glycerides formed from fatty acids having from $C_{13}$ to $C_{24}$ carbon atoms, with about 10 to 90 wt % of the fatty acids in the mixed glycerides being esterified within monoglycerides, and about 10 to 90 wt % of the fatty acids in the mixed glycerides being esterified within diesters; and (d) about 5-90 wt % of a surfactant which promotes self-emulsification.

In a second preferred embodiment there is provided in the first preferred embodiment an oral dosage form of cannabinoids, which further comprises about 10-30 wt % of free fatty acids having from $C_{13}$ to $C_{24}$ carbon atoms.

In a third preferred embodiment there is provided in the first preferred embodiment an oral dosage form of cannabinoids, wherein the one or more triglycerides and one or more mixed glycerides are present in a weight ratio of about 15:85 to 85:15, respectively.

In a fourth preferred embodiment there is provided in the first preferred embodiment an oral dosage form of cannabinoids, wherein the one or more triglycerides and one or more mixed glycerides are present in a weight ratio of about 30:70 to 70:30, respectively.

In a fifth preferred embodiment there is provided in the first preferred embodiment an oral dosage form of cannabinoids, wherein the one or more triglycerides and one or more mixed glycerides are present in a weight ratio of about 45:55 to 55:45, respectively.

In a sixth preferred embodiment there is provided in the first preferred embodiment an oral dosage form of cannabinoids, wherein the pharmacologically active cannabinoid is selected from the group consisting of tetrahydrocannabinol, $\Delta^9$-tetrahydrocannabinol (THC), $\Delta^8$-tetrahydrocannabinol, $\Delta^8$-tetrahydrocannabinol-DMH, $\Delta^9$-tetrahydrocannabinol propyl analogue (THCV), 11-hydroxy-tetrahydrocannabinol, 11-nor-9-carboxy-tetrahydrocannabinol, 5'-azido-$\Delta^8$-tetrahydrocannabinol, AMG-1, AMG-3, AM411, AM708, AM836, AM855, AM919, AM926, AM938, cannabidiol (CBD), cannabidiol propyl analogue (CBDV), cannabinol (CBN), cannabichromene, cannabichromene propyl analogue, cannabigerol, CP 47497, CP 55940, CP 55244, CP 50556, CT-3 (ajulemic acid), dimethylheptyl HHC, HU-210, HU-211, HU-308, WIN 55212-2, desacetyl-L-nantradol, dexanabinol, JWH-051, levonantradol, L-759633, nabilone, O-1184, and mixtures thereof.

In a seventh preferred embodiment there is provided in the first preferred embodiment an oral dosage form of cannabinoids, wherein the one or more triglycerides are selected from the group consisting of borage oil, coconut oil, cottonseed oil, soybean oil, safflower oil, sunflower oil, castor oil, corn oil, olive oil, palm oil, peanut oil, poppy seed oil, canola oil, hydrogenated soybean oil, hydrogenated vegetable oils, triolein, trilinolein, and trilinolenin.

In an eighth preferred embodiment there is provided in the first preferred embodiment an oral dosage form of cannabinoids, wherein the one or more mixed glycerides are selected from the group consisting of mixed glycerides esterified with long chain fatty acids, glyceryl behenate, glyceryl distearate, glyceryl isostearate, glyceryl laurate, glyceryl monooleate, glyceryl monolinoleate, glyceryl palmitate, glyceryl palmitostearate, glyceryl ricinoleate, glyceryl stearate, polyglyceryl 10-oleate, polyglyceryl 3-oleate, polyglyceryl 4-oleate, and polyglyceryl 10-tetralinoleate.

In a ninth preferred embodiment there is provided in the second preferred embodiment an oral dosage form of cannabinoids, wherein the one or more free fatty acids are selected from the group consisting of, behenic acid, lauric acid, linoleic acid, linolenic acid, myristic acid, palmitic acid, palmitoleic acid, palmitostearic acid, ricinoleic acid, stearic acid, soy fatty acids, oleic acid, and mixtures thereof.

In a tenth preferred embodiment there is provided in the first preferred embodiment an oral dosage form of cannabinoids wherein the surfactant is one or more selected from the group consisting of polyglycolized glycerides, polyoxyethylene glycerides, polyethylene glycol-fatty acid esters, polyethylene glycol glycerol fatty acid esters, transesterfication products of oils and alcohols, polyglycerized fatty acids, glycerol fatty acid esters, polyglycerol fatty acid esters, propylene glycol fatty acid esters, mono and diglycerides, polyethylene glycol sorbitan fatty acid esters, polyoxyethylene-polyoxypropylene block copolymers, sorbitan fatty acid esters, d-α-tocopheryl polyethylene glycol 1000 succinate, polyoxyethyleneglycol 660 12-hydroxystearate, polysorbates, and mixtures thereof.

In an eleventh preferred embodiment there is provided in the first preferred embodiment an oral dosage form of cannabinoids in a self-emulsifying system, wherein the surfactant is selected from the group consisting of almond oil PEG-6 esters, almond oil PEG-60 esters, apricot kernel oil PEG-6 esters, caprylic/capric triglycerides PEG-4 esters, caprylic/capric triglycerides PEG-4 complex, caprylic/capric glycerides PEG-6 esters, caprylic/capric glycerides PEG-8 esters, castor oil PEG-50 esters, hydrogenated castor oil PEG-5 esters, hydrogenated castor oil PEG-7 esters, 9 hydrogenated castor oil PEG-9 esters, corn oil PEG-6 esters, corn oil PEG-8 esters, corn glycerides PEG-60 esters, olive oil PEG-6 esters, hydrogenated palm/palm kernel oil PEG-6 esters, hydrogenated palm/palm kernel oil PEG-6 esters with palm kernel oil and PEG-6 and palm oil, palm kernel oil PEG-40 esters, peanut oil PEG-6 esters, glycerol esters of saturated C8-C18 fatty acids, glyceryl esters of saturated C12-C18 fatty acids, glyceryl laurate/PEG-32 laurate, glyceryl laurate glyceryl/PEG 20 laurate, glyceryl laurate glyceryl/PEG 32 laurate, glyceryl, laurate glyceryl/PEG 40 laurate, glyceryl oleate/PEG-20 glyceryl, glyceryl oleate/PEG-30 oleate, glyceryl palmitostearate/PEG-32 palmitostearate, glyceryl stearate/PEG stearate, glyceryl stearate/PEG-32 stearate, saturated polyglycolized glycerides, triisostearin PEG-6 esters, triolein PEG-6 esters, trioleate PEG-25 esters, polyoxyl 35 castor oil, polyoxyl 40 hydrogenated castor oil, polyoxyl 60 hydrogenated castor oil, PEG-8 caproate, PEG-8 caprylate, PEG-8 caprate PEG-8 laurate, PEG-8 oleate, PEG-8 stearate, PEG-9 caproate, PEG-9 caprylate, PEG-9 caprate PEG-9 laurate, PEG-9 oleate, PEG-9 stearate, PEG-10 caproate, PEG-10 caprylate, PEG-10 caprate PEG-10 laurate, PEG-10 oleate, PEG-10 stearate, PEG-10 laurate, PEG-12 oleate, PEG-15 oleate, PEG-20 laurate, PEG-20 oleate, caprylyic/capric glycerides, caprylate/caprate diglycerides, glyceryl monooleate, glyceryl ricinoleate, glyceryl laurate, glyceryl dilaurate, glyceryl dioleate, glyceryl mono/dioleate, glyceryl caprylate/caprate, medium chain C8/C10 mono- and diglycerides, mono- and diacetylated monoglycerides, polyglyceryl oleate, polyglyceryl-2 dioleate, polyglyceryl-10 trioleate, polyglyceryl-10 laurate, polyglyceryl-10 oleate, polyglyceryl-10 mono dioleate, propylene glycol caprylate/caprate, propylene glycol dicaprylate/dicaprate, propylene glycol monolaurate, propylene glycol ricinoleate, propylene glycol monooleate, propylene glycol dicaprylate/dicaprate, propylene glycol dioctanoate, PEG-20 sorbitan monolaurate, PEG-20 sorbitan monopalmitate, PEG-20 sorbitan monostearate, PEG-20 sorbitan monooleate, poloxamer 108, poloxamer 124, poloxamer 182, poloxamer 183, poloxamer 188, poloxamer 212, poloxamer 217, poloxamer 238, poloxamer 288, poloxamer 331, poloxamer 338, poloxamer 335, poloxamer 407, sorbitan monolaurate, sorbitan monopalmitate, sorbitan monoleate, sorbitan monostearate, sorbitan tristearate, d-α-tocopheryl polyethylene glycol 1000 succinate, polysorbate 20, polysorbate, polyethyleneglycol 660 12-hydroxystearate, and mixtures thereof.

In a twelfth preferred embodiment there is provided in a first preferred embodiment an oral dosage form of cannabinoids in a self emulsifying system, which further comprises cosolvents, solubilizing agents and antioxidants selected from the group consisting of ethanol, polyethylene glycol 300, polyethylene glycol 400, propylene glycol, propylene carbonate, N-methyl-2-pyrrolidones, dimethylacetamide, dimethyl sulfoxide, hydroxypropyl-β-cyclodextrins, sulfobutylether-β-cyclodextrin, α-cyclodextrin, HSPC phospholipid, DSPG phospholipid, DMPC phospholipid, DMPG phospholipid, ascorbyl palmitate, butylated hydroxy anisole, butylatedhydroxy anisole, propyl gallate, α-tocopherol, and γ-tocopherol, and mixtures thereof.

In a thirteenth preferred embodiment there is provided in the first and twelfth preferred embodiments an oral dosage form of cannabinoid, which further comprises:
 (e) about 1-80 wt % of solubilizing co-solvents; and
 (f) about 0.01-15 wt % of antioxidants.

In a fourteenth preferred embodiment there is provided in the first and twelfth preferred embodiments an oral dosage form of cannabinoid, which further comprises:
 (e) about 5-50 wt % of solubilizing co-solvent;
 (f) about 0.01-12.5 wt % of antioxidant.

In a fifteenth preferred embodiment there is provided in the first preferred embodiment an oral dosage form of cannabinoids, wherein the triglycerides contain from about 1 to 70 wt % of long chain fatty acids in the one and three position of the glyceride, and from about 30 to 99 wt % of long chain fatty acids at the two position of the glyceride, and the triglyceride contains from about 1 to 30 wt % of saturated fatty acids, and from about 70 to 99 wt % of unsaturated fatty acids.

In a sixteenth preferred embodiment there is provided in the first preferred embodiment an oral dosage form of cannabinoids, which further comprises about 2.5-15 wt % of a semi-solid inducer.

In a seventeenth preferred embodiment there is provided in the sixteenth preferred embodiment an oral dosage form of cannabinoids, wherein the semi-solid inducer is ascorbyl palmitate.

In an eighteenth preferred embodiment there is provided a method of avoiding and/or suppressing hepatic first pass metabolism of an orally administered cannabinoid after administration to the mammalian intestinal tract by targeted chylomicron/lipoprotein delivery in order to promote lymphatic transport, said method comprising orally administering said cannabinoid in an oral dosage form comprising:
 (a) about 1-90 wt % of a pharmacologically active form of cannabinoids;
 (b) about 15-85 wt % of one or more triglycerides formed from long chain fatty acids having from $C_{13}$ to $C_{24}$ carbon atoms, with about 5 to 95 wt % of said long chain fatty acids being polyunsaturated, and from about 5 to 95 wt % of said long chain fatty acids being monosaturated;
 (c) about 15-85 wt % of one or more mixed glycerides formed from fatty acids having from $C_{13}$ to $C_{24}$ carbon atoms, with about 10 to 90 wt % of the fatty acids in the mixed glycerides being esterified within monoglycerides, and about 10 to 90 wt % of the fatty acids in the mixed glycerides being esterified within diesters; and
 (d) about 5-90 wt % of a surfactant which promotes self-emulsification.

In a nineteenth preferred embodiment there is provided in the eighteenth preferred embodiment a method of avoiding and/or suppressing hepatic first pass metabolism of an orally administered cannabinoid after administration to the mammalian intestinal tract by targeted chylomicron/lipoprotein delivery in order to promote lymphatic transport, wherein the triglycerides contain from about 1 to 70 wt % of long chain fatty acids in the one and three position of the glyceride, and from about 30 to 99 wt % of long chain fatty acids at the two position of the glyceride, and the triglyceride contains from about 1 to 30 wt % of saturated fatty acids, and from about 70 to 99 wt % of unsaturated fatty acids.

In a twentieth preferred embodiment there is provided an oral dosage form of cannabinoids in a self-emulsifying system operable to avoid hepatic first pass metabolism via targeted chylomicron/lipoprotein delivery, thereby promoting lymphatic transport, said oral dosage form comprising:
 (a) about 1-90 wt % of a pharmacologically active form of cannabinoids;
 (b) about 15-85 wt % of one or more triglycerides formed from long chain fatty acids having from $C_{13}$ to $C_{24}$ carbon atoms, with about 5 to 95 wt % of said long chain fatty acids being polyunsaturated, and from about 5 to 95 wt % of said long chain fatty acids being monosaturated;
 (c) about 15-85 wt % of one or more mixed glycerides formed from fatty acids having from $C_{13}$ to $C_{24}$ carbon atoms, with about 10 to 90 wt % of the fatty acids in the mixed glycerides being monoglycerides, and about 10 to 90 wt % of the fatty acids in the mixed glycerides being diesters;
 (d) about 5-90 wt % of a surfactant which promotes self-emulsification, and wherein the triglycerides contain from about 1 to 70 wt % of long chain fatty acids in the one and three position of the glyceride, and from about 30 to 99 wt % of long chain fatty acids at the two position of the glyceride, and the triglycerides contain from about 1 to 30 wt % of saturated fatty acids, and from about 70 to 99 wt % of unsaturated fatty acids, and from about 70 to 99 wt % of the long chain fatty acids in the two position of the triglyceride are unsaturated and contain from about 1 to 3 double bonds, and from about 1 to 30 wt % of the fatty acids esterified in the mixed glycerides are saturated, and from about 70 to 99 wt % of the fatty acids esterified in the mixed glycerides are unsaturated.

DETAILED DESCRIPTION OF THE INVENTION

Figure 1:
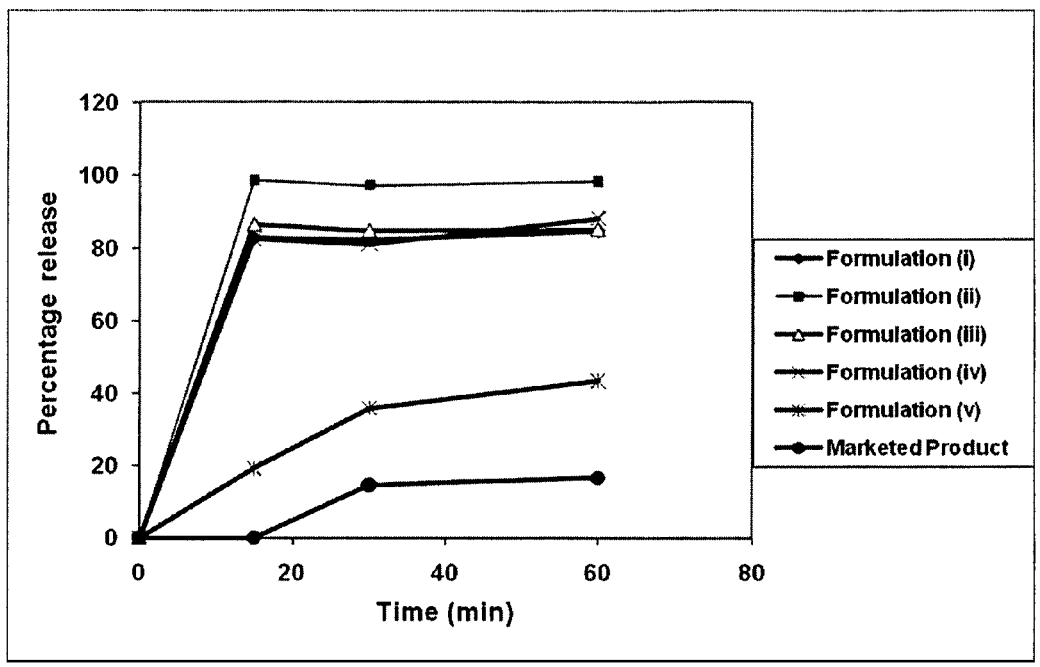
FIG. 1 is a graph showing dissolution profiles of cannabinoid containing formulations of the present invention, and a dissolution profile of a conventional cannabinoid containing formulation.

According to the present invention, improved dissolution, stability, and bioavailability of $\Delta^9$-THC is achieved by dissolving the $\Delta^9$-THC in an oily medium comprising triglycerides and/or mixed glycerides and/or medium/long chain saturated, mono-unsaturated, and poly-unsaturated fatty acids containing at least one surfactant component. This composition promotes self-emulsification, thereby promoting targeted chylomicron/lipoprotein delivery and optimal bioavailability after administration through the mammalian intestinal tract where endogenous bile salts reside.

Optionally, a preferred dosage form can include co-solvents, anti-oxidants, viscosity modifying agents, cytochrome P450 metabolic inhibitors, P-GP efflux inhibitors, and amphiphilic/non-amphiphilic solutes to induce semi-solid formation for targeted release rates.

In a preferred embodiment, to improve the solubility of the lipophilic drug, the oily medium of the formulation can be selected from the group consisting of one or more of longchain chain triglycerides or mixed glycerides including polyglycolized glycerides and polyoxyethylene glycerides, such as, anise oil, apricot kernel oil, apricot kernel oil PEG-6 esters, beeswax, borage oil, canola oil, castor oil, castor oil polyoxyl 35, castor oil polyoxyl 40, castor oil polyoxyl 40 hydrogenated, castor oil polyoxyl 60, castor oil polyoxyl 60 hydrogenated castor oil hydrogenated, cinnamon oil, clove oil, coconut oil, coconut oil-lecithin, coconut oil fractioned, coriander oil, corn oil, corn oil PEG-6 esters, corn oil PEG-8 esters, cottonseed oil, cottonseed oil hydrogenated, kernel oil, kernel oil PEG-6 esters, lemon oil, mineral oil, mineral oil (light), neutral oil, nutmeg oil, olive oil, olive oil PEG-6 esters, orange oil, palm kernel oil, palm kernel oil/hydrogenated, palm kernel oil PEG-6 esters, peanut oil, peanut oil PEG-6 esters, peppermint oil, poppy seed oil, safflower oil, sunflower oil, soybean oil, soybean oil hydrogenated, soybean oil refined, triisostearin PEG-6 esters, vegetable oil, vegetable oil hydrogenated, vegetable oils glyceride hydrogenated, vegetable oil PEG esters, triolein, trilinolein, trilinolenin, and mixtures thereof.

Other preferred oily mediums are long chain mono-, or di-, glycerides, and/or polyglycolized glycerides and polyoxyethylene glycerides, including glycerol esters of saturated C8-C18 fatty acids (Gelucire® 33/01), glyceryl esters of saturated C12-C18 fatty acids (Gelucire® 39/01 and 43/01), glyceryl behenate, glyceryl distearate, glyceryl isostearate, glyceryl laurate, glyceryl laurate/PEG-32 laurate (Gelucire® 44/14), glyceryl monooleate (Peceol®) and glyceryl monolinoleate (Maisine®), glyceryl palmitate, glyceryl palmitostearate, glyceryl palmitostearate/PEG-32 (Gelucire® 50/13) palmitostearate glyceryl ricinoleate, glyceryl stearate, glyceryl stearate/PEG stearate, glyceryl stearate/PEG-32 stearate (Gelucire® 53/10), glyceryl stearate/PEG-40 stearate, glyceryl stearate/PEG-75 stearate, glyceryl stearate/PEG-100 stearate, polyglyceryl 10-oleate, polyglyceryl 3-oleate, polyglyceryl 4-oleate, polyglyceryl 10-tetralinoleate, polyoxyl 100 glyceryl stearate, and saturated polyglycolized glycerides (Gelucire® 37/02 and Gelucire® 50/02), and mixtures thereof.

Other preferred oily mediums are long chain saturated fatty acids such as arachidic acid, behenic acid, 3-hydroxymyristic acid, lauric acid, lignoceric acid, mycoceranic acid, myristic acid, palmitic acid, phytanic acid, stearic acid, tuberculostearic acid, etc. Preferred long chain unsaturated fatty acids include arachidonic acid, linoleic acid, ($\alpha$ or $\gamma$ type), nervonic acid, oleic acid, palmitoleic acid, soy fatty acids, and mixtures thereof.

Preferred medium-chain mono-, di-, or tri-glycerides, including polyglycolized glyceride derivatives and polyoxyethylene glycerides, include caprylic/capric glycerides, caprylic/capric glycerides derived from coconut oil or palm seed oil (e.g. Labrafac®, Miglyol® 810, 812, Crodamol GTCC-PN, Softison® 378), propylene glycol caprylate/caprate (Labrafac® PC), propylene glycol dicaprylate/dicaprate (Miglyol® 840), medium chain (C8/C10) mono- and diglycerides (Capmul® MCM, Capmul® MCM (L)), and glycerol esters of saturated C8-C18 fatty acids (Gelucire® 33/01), and mixtures thereof.

Preferred medium chain fatty acids include caproic acid, caprylic acid, capric acid, and mixtures thereof.

Preferred fat-soluble vitamins and derivatives include vitamin A, vitamin E ($\alpha$ or $\gamma$ tocopherol), vitamin E PEG 1000 succinate (d-$\alpha$-tocopheryl polyethylene glycol 1000 succinate or TPGS), and mixtures thereof.

The surfactant component of the formulation can be used either alone or in combination with another surfactant to improve the self-emulsifying properties of the formulation. Preferred surfactant components are selected from the group consisting of polyglycolized glycerides and polyoxyethylene glycerides of medium to long chain mono-, di-, and triglycerides, such as: almond oil PEG-6 esters, almond oil PEG-60 esters, apricot kernel oil PEG-6 esters (Labrafil® M1944CS), caprylic/capric triglycerides PEG-4 esters (Labrafac® Hydro WL 1219), caprylic/capric triglycerides PEG-4 complex (Labrafac® Hydrophile), caprylic/capric glycerides PEG-6 esters (Softigen® 767), caprylic/capric glycerides PEG-8 esters (Labrasol®), castor oil PEG-50 esters, hydrogenated castor oil PEG-5 esters, hydrogenated castor oil PEG-7 esters, 9 hydrogenated castor oil PEG-9 esters, corn oil PEG-6 esters (Labrafil® M 2125 CS), corn oil PEG-8 esters (Labrafil® WL 2609 BS), corn glycerides PEG-60 esters, olive oil PEG-6 esters (Labrafil® M1980 CS), hydrogenated palm/palm kernel oil PEG-6 esters (Labrafil® M 2130 BS), hydrogenated palm/palm kernel oil PEG-6 esters with palm kernel oil, PEG-6, palm oil (Labrafil® M 2130 CS), palm kernel oil PEG-40 esters, peanut oil PEG-6 esters (Labrafil® M 1969 CS), glycerol esters of saturated C8-C18 fatty acids (Gelucire® 33/01), glyceryl esters of saturated C12-C18 fatty acids (Gelucire® 39/01 and 43/01), glyceryl laurate/PEG-32 laurate (Gelucire® 44/14), glyceryl laurate glyceryl/PEG 20 laurate, glyceryl laurate glyceryl/PEG 32 laurate, glyceryl, laurate glyceryl/PEG 40 laurate, glyceryl oleate/PEG-20 glyceryl, glyceryl oleate/PEG-30 oleate, glyceryl palmitostearate/PEG-32 palmitostearate (Gelucire® 50/13), glyceryl stearate/PEG stearate, glyceryl stearate/PEG-32 stearate (Gelucire® 53/10), saturated polyglycolized glycerides (Gelucire® 37/02 and Gelucire® 50/02), triisostearin PEG-6 esters (i.e. Labrafil® Isostearique), triolein PEG-6 esters, trioleate PEG-25 esters, polyoxyl 35 castor oil (Cremophor® EL), polyoxyl 40 hydrogenated castor oil (Cremophor® RH 40), polyoxyl 60 hydrogenated castor oil (Cremophor® RH60), and mixtures thereof.

Preferred polyglycolized derivatives and polyoxyethylene derivatives of medium to long chain fatty acids, which can be used in the present invention include PEG-8 caproate, PEG-8 caprylate, PEG-8 caprate PEG-8 laurate, PEG-8 oleate, PEG-8 stearate, PEG-9 caproate, PEG-9 caprylate, PEG-9 caprate PEG-9 laurate, PEG-9 oleate, PEG-9 stearate, PEG-10 caproate, PEG-10 caprylate, PEG-10 caprate PEG-10 laurate, PEG-10 oleate, PEG-10 stearate, PEG-10 laurate, PEG-12 oleate, PEG-15 oleate, PEG-20 laurate, PEG-20 oleate, and mixtures thereof.

Preferred glycerol, polyglycerol, and propylene glycol esters of medium to long chain fatty acids, which can be used in the present invention include caprylate/caprate diglycerides, glyceryl monooleate, glyceryl ricinoleate, glyceryl laurate, glyceryl dilaurate, glyceryl dioleate, glyceryl mono/dioleate, glyceryl caprylate/caprate, medium chain (C8/C10) mono- and diglycerides (Capmul® MCM, Capmul® MCM (L)), mono- and diacetylated monoglycerides, polyglyceryl oleate, polyglyceryl-2 dioleate, polyglyceryl-10 trioleate, polyglyceryl-10 laurate, polyglyceryl-10 oleate, and polyglyceryl-10 mono dioleate, propylene glycol caprylate/caprate (Labrafac® PC), propylene glycol dicaprylate/dicaprate (Miglyol® 840), propylene glycol monolaurate, propylene glycol ricinoleate, propylene glycol monooleate, propylene glycol dicaprylate/dicaprate, propylene glycol dioctanoate, and mixtures thereof.

Preferred polyethylene glycol sorbitan fatty acid esters, which can be used include PEG-20 sorbitan monolaurate, PEG-20 sorbitan monopalmitate, PEG-20 sorbitan monostearate, and PEG-20 sorbitan monooleate, and mixtures thereof.

Preferred polyoxyethylene-polyoxypropylene block copolymers, which can be used include poloxamers (108, 124, 182, 183, 188, 212, 217, 238, 288, 331, 338, 335, and 407), and mixtures thereof.

Preferred sorbitan fatty acid esters, which can be used include sorbitan monolaurate, sorbitan monopalmitate, sorbitan monoleate (Span® 20), sorbitan monostearate and sorbitan tristearate, and mixtures thereof.

Other preferred surfactants, which can be used include TPGS (d-α-tocopheryl polyethylene glycol 1000 succinate), polysorbate 20 (Tween® 20), polysorbate (Tween® 80), polyethyleneglycol 660 12-hydroxystearate (Solutol® HS-15), and mixtures thereof.

In a preferred embodiment, optional components of the formulation can include co-solvents, antioxidants, viscosity modifying agents, cytochrome P450 metabolic inhibitors, P-GP efflux inhibitors, and finally amphiphilic/non-amphiphilic solutes. These optional components can be used either alone or in combination with other ingredients to improve the chemical and physical properties of the self-emulsifying drug delivery systems.

Preferred co-solvents or solubilizers include agents such as ethanol, polyethylene glycol 300, polyethylene glycol 400, propylene glycol, propylene carbonate, N-methyl-2-pyrrolidones, dimethylacetamide, dimethyl sulfoxide, hydroxypropyl-β-cyclodextrins, sulfobutylether-β-cyclodextrin, α-cyclodextrin, glycerin, and various phospholipids (HSPC, DSPG, DMPC, & DMPG), and mixtures thereof.

Preferred antioxidants include ascorbyl palmitate, butylated hydroxy anisole, butylated hydroxy toluene, propyl gallate, α-tocopherol, and finally γ-tocopherol, etc. The antioxidants that can be chosen include combinations of two or more agents described above, whereby ascorbyl palmitate and tocopherol provide optimal synergistic effects.

Preferred viscosity modifying agents that can be used include unmodified starches, pregelatinized starches, crosslinked starches, guar gum, xanthan gum, acacia, tragacanth, carrageenans, alginates, chitosan, polyvinyl pyrrolidone (PVP, e.g. Kollidon®, Povidone®), polyethylene oxide (e.g. Polyox®), polyethylene glycols (PEGs, e.g. Carbowax®), polycarbophils (e.g. Carbopol®), Eudragit® series polymers (E, L, S, RL, RS, NE), hydroxymethylpropyl cellulose (HPMC), hydroxyethylcellulose (HEC), hydroxypropylmethylcelluose (HPC), carboxymethylcellose sodium (Na-CMC), ethylcellulose (e.g. Ethocel®), cellulose acetate, and cellulose acetate phthalate, polyvinylacetate/polyvinylpyrrolidone (PVA/PVP, e.g. Kollidon SR®), PVA/PEG graft copolymer (e.g. Kollidon IR®), hydrogenated vegetable oils, polyglycolized esters of fatty acids, carnauba wax, stearyl alcohol, and beeswax, and mixtures thereof.

Preferred cytochrome P450 inhibitors include any agent incorporated into the SEDDS matrix that inhibits pre-systemic hepatic first pass metabolism (i.e. first pass metabolism), such as d-α-tocopheryl polyethylene glycol 1000 succinate, anise oil, cinnamon oil, coriander oil, grapefruit oil, lemon oil, orange oil, peppermint oil, ascorbyl palmitate, propyl gallate, and various combinations thereof.

Preferred PGP efflux inhibitors include any agent incorporated into the SEDDS matrix that inhibits PGP induced cellular efflux mechanisms (i.e. MDR), such as polyethoxylated castor oil derivatives, polyoxyethylene sorbitan monooleate, polyoxyethylene glycerides, and various combinations thereof.

Preferred amphiphilic/non-amphiphilic solutes include any agent incorporated into the SEDDS matrix that induces semi-solid formation from a liquid state. Preferably, these agents would be pharmaceutical grade powder materials, which are water insoluble (e.g. Ascorbyl Palmitate).

In a preferred embodiment, $\Delta^9$-THC or any other cannabinoid class compound can be directly incorporated into a commercially available proprietary blend of excipients, surfactants, cosurfactants, and a lipid phase. These proprietary blends known as SMEDDS® (available from Gattefosse Corporation) are self-emulsifying matrixes which achieve improved dissolution and bioavailability of lipophilic compounds. Optional components can also be added such as co-solvents, antioxidants, viscosity modifying agents, cytochrome P450 metabolic inhibitors, P-GP efflux inhibitors, and amphiphilic/non-amphiphilic solutes.

In a preferred embodiment, the proportions of the ingredients in the composition of the present invention include from about 1-90 wt %, preferably from about 1-80 wt %, and more preferably from about 1-60 wt % of an active cannabinoid; from about 5-90 wt %, preferably from about 10-80 wt %, more preferably from about 20-80 wt % of an oily medium; and from about 5-90 wt %, preferably from about 10-80 wt %, more preferably from about 20 to 60 wt % of the surfactant component;

The optional solubilizing and co-solvent amounts vary from about 1-80 wt %, preferably from about 5-50 wt %; more preferably from about 10-50 wt %.

The optional antioxidants may vary from about 0.01-15 wt %, preferably from about 0.5 to 12.5 wt %.

In a preferred embodiment, the semi-solid inducer amount, which transforms the liquid SEDDS matrix to a semi-solid SEDDS matrix, varies from about 2.5-15 wt %, preferably from about 5-10 wt %, more preferably from about 7.5 to 10 wt %.

Direct filling of hot melt matrices into hard gelatin capsules can be performed in the case of self-emulsifying drug delivery systems. The vehicles (hard gelatin capsules) act as dispersing or emulsifying agents for the liberated drug in a finely divided state. The higher surface area of a drug produced in this way facilitates dissolution in the gastrointestinal fluid, especially in the presence of bile salts, lecithin, and lipid digestion mixtures.

For ease of manufacturing, the carrier must be amenable to liquid filling into hard gelatin capsules as hot melt matrices. The melting temperatures of carrier solutions preferably do not exceed above 80° C., which is the maximum acceptable temperature for hard gelatin capsule shells. This preferred approach has been followed in filling preferred formulations of the present invention.

Appropriate in vitro dissolution testing can be used to predict therapeutic performance of any liquid, and semisolid oral dosage forms in order to ensure product quality and batch-to-batch consistency. Optimal dissolution testing methodologies clarify dissolution testing of self-emulsifying drug delivery formulations intended for gastrointestinal delivery. Thermal and textural properties, as well as viscosity and consistency of the dosage form, can be used to influence drug release from lipid-based formulations.

In addition, it has been shown that changes in dissolution rate on aging do not always correlate with changes in bioavailability from lipid-based formulations. Consequently, in order to achieve more meaningful results during dissolution testing, SEDDS are analyzed under simulated gastric and intestinal conditions under fed and fasted states. This is in addition to conventional dissolution testing in aqueous media with the presence of various surfactants.

In the present invention, the compositions are initially tested under various dissolution media having different surfactant concentrations (1-5% w/w of sodium lauryl sulfate, TritonX-100, and Polysorbate 80) in order to identify ideal conditions for routine analysis. These compositions are also evaluated against the commercial product to predict better in vivo release profile. Thereafter, stability testing for SEDDS formulations is peculiar due to the presence of lipophilic compounds and lipid excipients are carried out. Thus, monitoring the stability of excipients is important in addition to the active ingredient.

Capsule leakage is a common problem and sophisticated detection systems are often employed to monitor such leakage. In order to maintain the product integrity and closure from the surrounding environment, the capsule dosage form resulting from the use of SEDDS in the present invention is anticipated to be in either a soft gelatin form, hard gelatin with band-sealed, hard gelatin with solvent sealing (e.g. Capsugel's Licaps). Band sealing, for instance, utilizes a sealing solution containing gelatin. This composition is preferably maintained at 45-48° C. for a nice band formation around a capsule to prevent any leakage or accidental opening of the product.

In the present invention various cannabinoids can be used alone or in combination to achieve synergistic effects. Suitable cannabinoid compounds which can be used either alone or in combination include tetrahydrocannabinol, $\Delta^9$-tetrahydrocannabinol (THC), $\Delta^8$-tetrahydrocannabinol, $\Delta^8$-tetrahydrocannabinol-DMH, $\Delta^9$-tetrahydrocannabinol propyl analogue (THCV), 11-hydroxy-tetrahydrocannabinol, 11-nor-9-carboxy-tetrahydrocannabinol, 5'-azido-$\Delta^8$-tetrahydrocannabinol, AMG-1, AMG-3, AM411, AM708, AM836, AM855, AM919, AM926, AM938, cannabidiol (CBD), cannabidiol propyl analogue (CBDV), cannabinol (CBN), cannabichromene, cannabichromene propyl analogue, cannabigerol, CP 47497, CP 55940, CP 55244, CP 50556, CT-3 (ajulemic acid), dimethylheptyl HHC, HU-210, HU-211, HU-308, WIN 55212-2, desacetyl-L-nantradol, dexanabinol, JWH-051, levonantradol, L-759633, nabilone, O-1184. This invention also extends to other agents with homologous structural characteristics common with the cannabinoid class of compounds.

The proposed SEDDS compositions of the present invention are also useful to improve the dissolution, bioavailability, and stability of various lipophilic drugs having poor aqueous solubility. These agents can belong to drugs categories such as analgesics, antihelminthics, antiarrhythmic, antiasthma, antibacterial, antiviral, anticoagulants, antidepressants, antidiabetics, antiepileptics, antifungal, antigout, antihypertensive, antimalarials, antimigraine, antimuscarinic, antineoplastic, antiprotozoal, antithyroid, antitussives, anxiolytics, sedatives, hypnotics, neuroleptics, cardiac inotropics, corticosteroids, diuretics, antiparkinsonian, gastrointestinal, antihistamines, keratolytics, lipid regulating agents, muscle relaxants, antianginal, nutritional, sex hormones, and stimulants.

EXAMPLES

The following examples illustrate formulations, dissolution methodology, and physical-chemical stability evaluations. However, the following examples are intended to be exemplary only and in no way limit the scope of the present invention. The listed ingredients can be suitably replaced with similar excipients known in the art.

A list of materials used in the Examples and the source of these materials is as follows:

(i) $\Delta^9$-THC (National Institute on Drug Abuse, Rockville, Md.)

(ii) Oleic Acid, Super Refined (Croda, USA)

(iii) Peppermint Oil (iv) Sesame Oil, Super Refined (Croda, USA)

(v) Soybean Oil, Super Refined (Croda, USA)

(vi) Capmul MCM (L) (Abitec Corp., USA) (vii) Cremophor EL (BASF, Germany)

(viii) Cremophor RH 40 (BASF, Germany)

(ix) Labrasol (Gattefosse, USA)

(x) Labrafil M1944 CS (Gattefosse, USA)

(xi) Maisine 35-1 (Gattefosse, USA)

(xii) Ascorbyl Palmitate (Spectrum Chemicals, USA)

(xiii) Vitamin E, FCC (Spectrum Chemicals, USA)

(xiv) Povidone K-30 (BASF, Germany)

(xv) Ethanol, USP, 200 Proof (Aaper Chemicals, USA)

Example 1

Tests were conducted to determine the feasibility of applying Type I and Type II self-emulsifying drug delivery systems for $\Delta^9$-THC, as well as for improving dissolution testing over the existing sesame oil based compositions (i.e. Marinol®). Based on initial results, it was found that Type III self-emulsifying drug delivery systems could be used with the addition of hydrophilic co-solvents (e.g. ethanol). The formulations tested to improve the dissolution of $\Delta^9$-THC are shown in Table 1 below. The required amounts of excipients included therein, along with $\Delta^9$-THC (resin form), were transferred to the test tube and were sonicated for 30-45 min (temperature not more than 50° C.) until a clear solution was obtained. The solutions of the respective formulations were filled into size "1" hard gelatin capsules. It was later found that heat could be applied to the formulation processing steps to improve formulation content uniformity and homogeneity.

TABLE 1

| Composition | mg of ingredient per formulation (% per caps) | | | | | | |
|---|---|---|---|---|---|---|---|
| | (i) | (ii) | (iii) | (iv) | (v) | (vi) | (vii) |
| $\Delta^9$-THC (in resin form) | 10 (3.85) | 10 (3.85) | 10 (3.85) | 10 (3.85) | 10 (3.65) | 10 (3.71) | 10 (4.1) |
| Oleic acid | — | 125 (48.1) | 125 (48.1) | 62 (24) | — | — | 235 (95.95) |
| Capmul MCM (L) | 250 (96.15) | — | — | — | — | — | — |
| Labrasol | — | 125 (48.1) | — | — | — | 131.5 (48.88) | — |
| Labrafil M 1944CS | — | — | 125 (48.1) | 188 (72.16) | 139 (50.70) | — | — |
| Sesame Oil | — | — | — | — | 125 (45.65) | — | — |
| Soybean Oil | — | — | — | — | — | 127.5 (47.41) | — |
| Total | 260 (100) | 260 (100) | 260 (100) | 260 (100) | 274 (100) | 269 (100) | 245 (100) |

FIG. 1 shows that the tested formulations proved to be more optimal than commercial formulations. These dissolution studies where conducted using 2% SLS in water media (Paddle Apparatus, 75 rpm). These tests also established that it was possible to enhance the dissolution of $\Delta^9$-THC using self-emulsifying drug delivery systems.

Example 2

The above prepared formulation vii (Table 1), which was categorized as a Type I SEDDS system, was evaluated in various dissolution medium at 37° C. (paddle, 75 RPM) in order to determine the most appropriate testing conditions. The percentage release obtained in each of the tested dissolution medium is set forth in Table 2.

TABLE 2

| | Percentage release (min) | | | | |
|---|---|---|---|---|---|
| Dissolution medium | 15 | 30 | 60 | 120 | 240 |
| Water | 0 | 0 | 0 | 0.3 | 1.1 |
| 2% SLS in Water | ≥100.0 | ≥100.0 | ≥100.0 | ≥100.0 | ≥100.0 |
| 5% TritonX-100 | 67.5 | ≥100.0 | ≥100.0 | ≥100.0 | ≥100.0 |
| Acetate buffer, pH 4.5 | 0.0 | 0.0 | 0.0 | 0.0 | 0.0 |
| Borate buffer, pH 9.5 | 39.8 | 67.3 | ≥100.0 | ≥100.0 | ≥100.0 |
| 0.1N HCl | 0.0 | 0.0 | 0.0 | 0.0 | 0.0 |

It is evident from the above results in Table 2 that 2% SLS or 5% TritonX-100 is an ideal choice for evaluating the $\Delta^9$-THC SEDDS formulations. Additional media such as simulated gastric and intestinal media may be required for further evaluation. In particular, fasted state simulated intestinal media (FaSSIF) and fed state simulated intestinal media (FeSSIF) are preferably used.

The data in Table 2 also establishes that SEDDS systems have a protective effect for $\Delta^9$-THC against acid catalyzed degradation in the stomach environment. This is due to the fact that the drug is retained within the SEDDS matrix upon initial dilution in aqueous media and is unavailable for release into the surrounding media. Upon performing aqueous dilution tests for placebo formulations described below (Examples 3 & 4), the formation of dispersions further show that SEDDS systems protect active cannabinoids against acid catalyzed degradation in the stomach (Example 5).

Example 3

Preferred Type I, Type II, and Type III SEDDS systems are isotropic in nature with uniform phase behavior before dilution in aqueous media. Phase separated SEDDS formulae, are not isotropic in nature and demonstrate cracking or poor matrix uniformity in the case of semi-solids.

Table 3 below shows the results of phase behavior examinations for select SEDDS, placebo formulations utilizing combinations of an oily carrier medium with Cremophor EL. Examinations were macroscopic (i.e. visual) as well as microscopic (Olympus™ Stereomicroscope).

TABLE 3

| Ingredient | (a) mg (%) | (b) mg (%) | (c) mg (%) | (d) mg (%) |
|---|---|---|---|---|
| PHYSICAL STATE | Liquid | Liquid | Fluidic Semi-Solid | Semi-Solid |
| Active Agent | 0 (3.85) | 0 (3.85) | 0 (3.85) | 0 (3.85) |
| Oil Component/Fatty Acid Carrier (e.g. Oleic Acid) | 120.0 (46.15) | 121.75 (46.8) | 158.0 (60.8) | 112.5 (43.1) |
| Surfactant Component (e.g. Cremophor EL) | 120.0 (46.15) | 121.75 (46.8) | 79.0 (30.4) | 112.5 (43.1) |
| Vitamin E, FCC | 5.0 (1.925) | — | — | — |
| Ascorbyl Palmitate | 5.0 (1.925) | 6.5 (2.5) | 13.0 (5.0) | 26.0 (10.0) |
| Total* | 250 (100) | 250 (100) | 250 (100) | 251 (100) |

*Percentages in "( )" are based on the fill weight of ~260 mg for all drug loaded formulations Table 3 shows that with increasing ascorbyl palmitate concentrations, the SEDDS matrix changes from liquid state to a fluidic semi-solid state or semi-solid state. Thus, ascorbyl palmitate, an amphiphilic solute, serves as a semi-solid inducer when present in excess concentrations in the SEDDS formulation matrix.

In the present example, the oily carrier medium is replaced by various "oils". The surfactant component is replaced by various ingredients. Additional ingredients in the SEDDS matrix include viscosity modifiers, antioxidants, and metabolic/PGP inhibitors. When SEDDS matrices are administered with or without a capsule shell to a mammalian gastrointestinal system (see Example 5), the following apply:

(i) The initial aqueous dispersion of the SEDDS systems in the acidic stomach contents result in protection against the acidic climate.

(ii) With the presence of bile salts in the upper duodenum, the SEDDS dosage form contents are incorporated into mammalian lipid absorption pathways (i.e., lymphatic transport), thereby bypassing hepatic first-pass metabolism.

(iii) When comparing the liquid SEDDS versus the semi-solid SEDDS compositions due to higher concentration of amphiphilic/non-amphiphilic, the former system provides faster drug dissolution profiles, whereas the latter system provides more prolonged dissolution profiles, respectively.

(iv) Liquid SEDDS systems immediately release dosage forms, whereas semi-solid SEDDS systems sustain release dosage forms.

Example 4

Preferred Type I, Type II, and Type III SEDDS systems are isotropic in nature with uniform phase behavior before dilution in aqueous media. Phase separated SEDDS formulae, which are not isotropic in nature, demonstrate cracking or poor matrix uniformity in the case of semi-solids.

Table 4 below provides the results of phase behavior examinations for select SEDDS, placebo formulations utilizing combinations of an oily carrier medium with Labrasol. Examinations were macroscopic (i.e. visual) as well as microscopic (Olympus™ Stereomicroscope).

TABLE 4

| Ingredient | (e) mg (%) | (f) mg (%) | (g) mg (%) |
|---|---|---|---|
| PHYSICAL STATE | Liquid | Fluidic Semi-Solid | Semi-Solid |
| Active Agent | 0 (3.85) | 0 (3.85) | 0 (3.85) |
| Oil Component/ Fatty Acid Carrier (e.g. Oleic Acid) | 121.75 (46.8) | 158.0 (60.8) | 112.5 (43.1) |
| Surfactant Component (e.g. Labrasol) | 121.75 (46.8) | 79.0 (30.4) | 112.5 (43.1) |
| Ascorbyl Palmitate | 6.5 (2.5) | 13.0 (5.0) | 26.0 (10.0) |
| Total* | 250 (100) | 250 (100) | 251 (100) |

*Percentages in "( )" are based on the fill weight of ~260 mg for all drug loaded formulations It can be seen from Table 3 that with increasing ascorbyl palmitate concentrations, the SEDDS matrix changes from a liquid state to a fluidic semi-solid state or a semi-solid state, etc. Thus, ascorbyl palmitate, an amphiphilic solute, serves as a semi-solid inducer when present in excess concentrations in the SEDDS formulation matrix.

In the present example, the oily carrier medium is replaced by various "oils" and the surfactant component replaced by various ingredients as previously described above. Additional optional ingredients are present in the SEDDS matrix (e.g. viscosity modifiers, antioxidants, metabolic/PGP inhibitors, etc.)

The following conditions apply when SEDDS matrices are administered with or without a capsule shell to a mammalian gastrointestinal system (see Example 5):

(i) The initial aqueous dispersion of the SEDDS systems in the acidic stomach contents result in protection against the acidic climate.

(ii) With the presence of bile salts in the upper duodenum, the SEDDS dosage form contents are incorporated into mammalian lipid absorption pathways (i.e., lymphatic transport), thereby bypassing hepatic first-pass metabolism.

(iii) When comparing the liquid SEDDS versus the semi-solid SEDDS compositions due to higher concentration of amphiphilic/non-amphiphilic, the former system would provide faster drug dissolution profiles whereas the latter system would provide more prolonged dissolution profiles, respectively.

(iv) Liquid SEDDS systems are immediately released and semi-solid SEDDS systems undergo sustained release.

Example 5

The present invention provides $\Delta^9$-THC SEDDS compositions (i.e. Types I, II, & III) that form dispersions upon initial dilution in an aqueous environment. With the presence of bile salts in the upper intestinal lumen, the dispersion components resulting from the disintegration of the dosage form are incorporated into lipid absorption pathways (i.e. chylomicron/lipoprotein assembly to promote lymphatic transport and to avoid hepatic first-pass metabolism).

To test these possible outcomes, dispersion tests were conducted in both aqueous and surfactant media. Table 5 below provides the results of aqueous dispersion tests of placebo formulations previously described in Examples 3 and 4. In addition, dispersion tests were conducted on select placebo compositions based on the original SEDDS formulae presented in Example 1.

Approximately 25 mg of each placebo formulation was added to 90 mL of selected media in a beaker with stir bar at 37° C. This procedure was designed to simulate USP Type II dissolution testing conditions employed in Example 1.

TABLE 5

| Observations of Dispersion Testing after 1 Hour | Dispersion Media | | |
|---|---|---|---|
| | 2% SLS (Surfactant Dispersion) | Water (Aqueous Dispersion) | Dilution of Aqueous Dispersion into 2% SLS Surfactant Bath (5x) |
| (a) from Table 3 | Clear Solution with No Visible Particulates | Cloudy Dispersion with Particulates Visible | Cloudy Dispersion Previously Observed Becomes Clear Solution |
| (e) from Table 4 | Clear Solution with No Visible Particulates | Cloudy Dispersion with Particulates Visible | Cloudy Dispersion Previously Observed Becomes Clear Solution |
| (i) from Table 1 | Clear Solution with No Visible Particulates | Fine Cloudy Dispersion with Particulates Visible | Cloudy Dispersion Previously Observed Becomes Clear Solution |

The dispersion testing results further support anticipated results when $\Delta^9$-THC SEDDS compositions are administered to a mammalian gastrointestinal system. Based on Table 5, the following outcomes apply:

(i) The initial aqueous dispersions of the SEDDS systems in the acidic stomach contents result in protection against the acidic climate, and (ii) In the presence of bile salts in the upper duodenum, the SEDDS dosage form contents are incorporated into mammalian lipid absorption pathways (i.e., lymphatic transport), thereby bypassing hepatic first-pass metabolism.

The results illustrated in Examples 1-5 provide encouraging results of optimization of $\Delta^9$-THC SEDDS compositions. Further efforts demonstrated in subsequent examples emphasize the modulation of drug release rates by excipient selection as well as chemical stabilization of SEDDS compositions by incorporating synergistic antioxidant combinations.

Example 6

Based on initial compositions (Table 1) as well as information in U.S. Pat. No. 6,232,333, additional $\Delta^9$-THC SEDDS compositions are tested to evaluate the effect of changing oil:surfactant ratios on dissolution properties in 2% SLS media (see Example 2). The resultant formulation matrices are evaluated to ascertain if they perform as immediate release products. Table 6 summarizes the compositions evaluated in Example 6. The basic procedures to be employed for the preparation of these SEDDS combinations include:

(i) Transfer Oil and Surfactant components into a clean beaker and heating the ingredients to 50° C.;

(ii) Slowly adding Ascorbyl Palmitate to the mixture;

(iii) Stirring the contents well to form a homogeneous mixture and continuing to maintain solution at 50-55° C.;

(iv) Adding the required quantity of $\Delta^9$-THC into the above melt matrix slowly under stirring and continue heating at 50-55° C. until it dissolves/melts to form a homogeneous formulation matrix; and (v) Filling the formulation matrix with the help of a pipette into a capsule size "1 as per the target weight, and allowing to cool to room temperature.

TABLE 6

| | Composition mg of ingredient per formulation (% per caps) | | | |
|---|---|---|---|---|
| | #1 | #2 | #3 | #4 |
| $\Delta^9$-THC (in resin form) | 10 (3.85) | 10 (3.85) | 10 (3.85) | 10 (3.85) |
| Oil Component (Oleic acid) | 121.75 (46.8) | 181.75 (69.9) | 121.75 (46.8) | 181.75 (69.9) |
| Surfactant (Cremophor RH40) | 121.75 (46.8) | 61.75 (23.75) | — | — |
| Surfactant (Labrasol) | — | — | 121.75 (46.8) | 61.75 (23.75) |
| Ascorbyl Palmitate | 6.5 (2.5) | 6.5 (2.5) | 6.5 (2.5) | 6.5 (2.5) |
| Total | 260 (100) | 260 (100) | 260 (100) | 260 (100) |

The variations in oil to surfactant ratios do not adversely impact the dissolution test results. For, Formulation #s 1, 2, 3, & 4 as shown in Table 6, dissolution of the active agent in 2% SLS is nearly complete within 1 hour (paddle, 75 RPM). These results are similar to the SEDDS compositions described in Table 1 and FIG. 1. It is noted that formulations prepared under Example 6 are characterized as liquid SEDDS compositions.

Example 7

Based on initial compositions (Table 1) as well as information obtained from U.S. Pat. No. 6,008,228, additional compositions are tested to evaluate the efficacy of supersaturable SEDDS systems with the addition of viscosity modifying agents. These supersaturable SEDDS systems are evaluated for improvements in $\Delta^9$ dissolution profiles in 2% SLS media when compared to Marinol® dissolution (FIG. 1). It is noted that Capmul MCM (L) serves as both the oil and surfactant components of the SEDDS systems. This polyfunctional pharmaceutical excipient contains multiple ingredients, especially medium chain mono and diglycerides. The resultant formulation matrices performed as immediate release products.

Table 7 summarizes the compositions listed in Example 7. The basic procedures to be employed for the preparation of these SEDDS combinations include:
(i) Transferring Capmul MCM (L) and Povidone K-30 into a clean beaker and heating the ingredients to 50° C.;
(ii) Slowly adding Ascorbyl Palmitate or DL-α-Tocopherol to the preceding mixture;
(iii) Stirring the contents well to form a homogeneous mixture and continuing to maintain solution at 50-55° C.;
(iv) Adding the required quantity of $\Delta^9$-THC into the above melt matrix slowly under stirring and continue heating at 50-55° C. until it dissolves/melts to form a homogeneous formulation matrix; and
(v) Filling the formulation matrix with the help of a pipette into a capsule size "1" as per the target weight and allowing to cool to room temperature to form a semi-solid matrix.

TABLE 7

| | Composition mg of ingredient per formulation (% per caps) | | | |
|---|---|---|---|---|
| | #5 | #11 | #6 | #12 |
| $\Delta^9$-THC (in resin form) | 10 (3.85) | 10 (3.85) | 10 (3.85) | 10 (3.85) |
| Oil/Surfactant Component (Capmul MCM (L)) | 223.5 (85.95) | 223.5 (85.95) | 217.0 (83.45) | 217.0 (83.45) |
| PVP K-30 (Povidone) | 20 (7.70) | 20 (7.70) | 20 (7.70) | 20 (7.70) |
| DL-α-Tocopherol | — | 6.5 (2.5) | — | 13.0 (5.0) |
| Ascorbyl Palmitate | 6.5 (2.5) | — | 13.0 (5.0) | — |
| Total | 260 (100) | 260 (100) | 260 (100) | 260 (100) |

* Capmul based compositions based on commercial Saquinivir (Fortovase) formulae as described in U.S. Pat. No. 6,008,228

The variations in antioxidant type or concentrations (i.e. Ascorbyl Palmitate or DL-α-Tocopherol) do not drastically alter the dissolution testing profiles for these supersaturable SEDDS formulation (i.e. #s 5, 6, 11 & 12 as shown in Table 7). The profiles for these formulations in 2% SLS were, however, peculiarly different from profiles for the initial compositions (i.e. FIG. 1).

Figure 2:
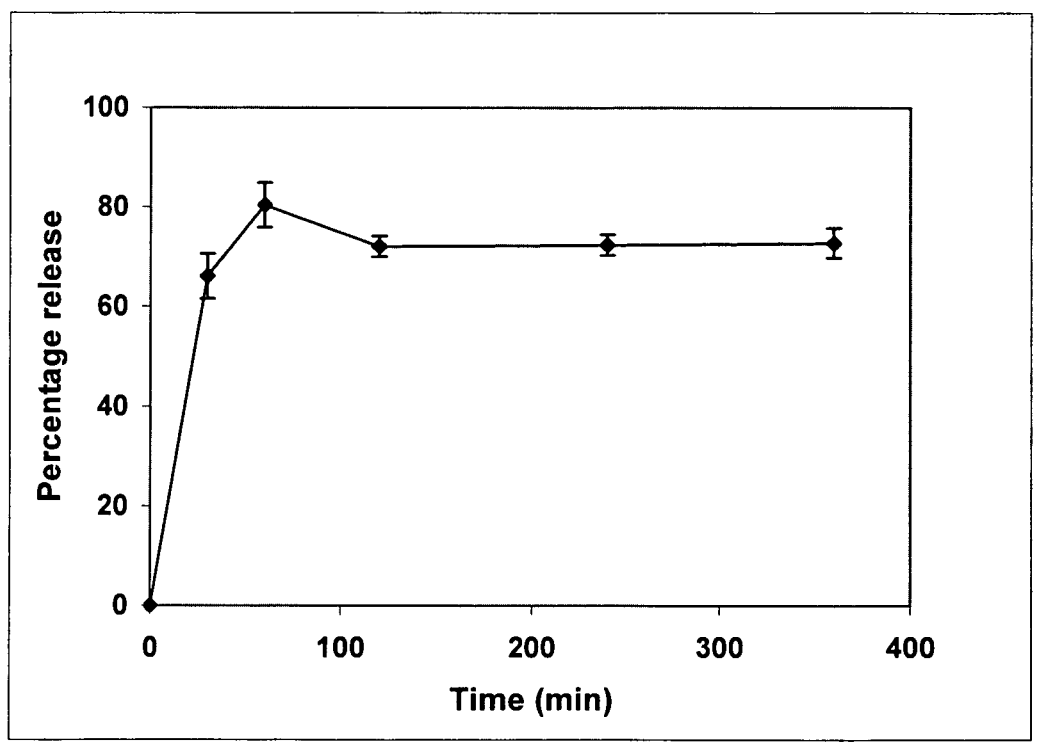
FIG. 2 is a graph showing the dissolution profile of a cannabinoid containing formulation of the present invention illustrating, in particular, the peak concentration and plateau region of the dissolution profile.

As for Formulation #5 as presented in Table 7, the dissolution results are illustrated in FIG. 2, whereby the initial dispersion provides a supersaturable peak concentration. This is analogous to a situation observed with amorphous drug dissolution profiles. In either case, a plateau region occurs after initial supersaturation.

Example 8

Based on initial compositions (Table 1), additional $\Delta^9$-THC SEDDS compositions are tested to evaluate the effect of varying the oily medium (i.e. from oleic acid to soybean oil) on dissolution properties in 2% SLS media (see Example 2). The resultant formulation matrices perform as immediate release products.

Table 8 summarizes the compositions in Example 8. The basic procedures to be employed for the preparation of these SEDDS combinations include:
(i) Transferring Oil and Surfactant components into a clean beaker and heating the ingredients to 50° C.;
(ii) Slowly adding Ascorbyl Palmitate to the mixture;
(iii) Stirring the contents well to form a homogeneous mixture and continuing to maintain solution at 50-55° C.;
(iv) Adding the required quantity of $\Delta^9$-THC into the above melt matrix slowly under stirring and continuing heating at 50-55° C. until it dissolves/melts to form a homogeneous formulation matrix; and
(v) Filling the formulation matrix with the help of a pipette into a capsule size "1 as per the target weight and allowing to cool to room temperature.

TABLE 8

| | Composition mg of ingredient per formulation (% per caps) | |
|---|---|---|
| | #7 | #8 |
| $\Delta^9$-THC (in resin form) | 10 (3.85) | 10 (3.85) |
| Oil Component (Soybean Oil) | 121.75 (46.8) | 181.75 (69.9) |

TABLE 8-continued

| | Composition mg of ingredient per formulation (% per caps) | |
|---|---|---|
| | #7 | #8 |
| Surfactant Component (Cremophor RH40) | 121.75 (46.8) | 61.75 (23.75) |
| Ascorbyl Palmitate | 6.5 (2.5) | 6.5 (2.5) |
| Total | 260 (100) | 260 (100) |

The variations in oily medium do not alter the release profile pattern as previously described with the original compositions. The dissolution process is nearly complete within 1 hour in 2% SLS media (paddle, 75 RPM).

Example 9

Based on initial compositions (Table 1) as well as information obtained from Examples 3 and 4, additional $\Delta^9$-THC SEDDS compositions are tested with high ascorbyl palmitate content loading for semi-solid formation. The resultant formulation matrices perform as sustained release products. Table 9 summarizes the compositions evaluated in Example 9. The basic procedures to be employed for the preparation of these SEDDS combinations include:

(i) Transferring $\Delta^9$-THC into a clean beaker and heating the ingredients to 65-70° C.;
(ii) Slowly adding the oil component to the beaker;
(iii) Adding surfactant component to the clear mixture;
(iv) Stirring the contents well to form a homogeneous mixture and continuing to maintain the clear mixture at 65-70° C.;
(v) Adding the required quantity of Ascorbyl Palmitate into the above melt matrix slowly under stirring and continuing heating at 65-70° C. until it dissolves/melts to form a homogeneous formulation matrix; and
(vi) Filling the formulation matrix with the help of a pipette into a capsule size "1 as per the target weight and allowing to cool to room temperature to form a semi-solid matrix or liquid.

(ii) Slowly adding the oil component to the beaker;
(iii) Add surfactant component to the clear mixture;
(iv) Stirring the contents well to form a homogeneous mixture and continuing to maintain the clear mixture at 65-70° C.;
(v) Adding the required quantity of Ascorbyl Palmitate into the above melt matrix slowly under stirring and continuing heating at 65-70° C. until it dissolves/melts to form a homogeneous formulation matrix; and
(vi) Filling the formulation matrix with the help of a pipette into capsule size "1" (hypromellose or hard gelatin) as per the target weight and allow to cool to room temperature to form a semi-solid matrix or liquid.

TABLE 9

| | Composition mg of ingredient per placebo formulation (% per caps) | | | |
|---|---|---|---|---|
| | #13 | #14 | #15 | #16 |
| Active Agent | 10 (3.85) | 10 (3.85) | 10 (3.85) | 0 (3.85) |
| Oil Component (Oleic acid) | 150.0 (57.47) | 150.0 (57.47) | | |
| Oil Component (Soybean Oil) | | | 150.0 (57.47) | 150.0 (57.47) |
| Surfactant Component (Cremophor RH40) | 75.0 (28.74) | — | 75.0 (28.74) | — |
| Surfactant Component (Labrasol) | — | 75.0 (28.74) | — | 75.0 (28.74) |
| Ascorbyl Palmitate | 26.0 (9.96) | 26.0 (9.96) | 26.0 (9.96) | 26.0 (9.96) |
| Total* | 261 (100) | 261 (100) | 261 (100) | 261 (100) |

The incorporation of high ascorbyl palmitate concentrations results in sustained drug release pattern over a 4 to 6 hour period in 2% SLS media (paddle, 75 RPM). The prolonged drug release rates are attributed to the formation of a semi-solid matrix. The semi-solid matrix induced by the ascorbyl palmitate serves as a stabilizing mechanism for a compound such as $\Delta^9$-THC, which demonstrates a high oxidation potential. Finally, it is realized during formulation preparation that processing temperatures can reach as high as 65-70° C. This does not adversely impact the chemical and physical characteristics of the $\Delta^9$-THC SEDDS matrices.

Example 10

Based on initial compositions (Table 1) as well as information obtained from Example 6, additional $\Delta^9$-THC SEDDS compositions are evaluated with different surfactant components (i.e. Cremophor EL, Labrafil M1944CS). In addition, combinations of surfactants are tested in order to obtain a composite HLB value of approximately between 11-12 for optimal performance of a Type II SEDDS system. Finally, combinations of antioxidants are tested in order to optimize synergistic protection for the drug compound and SEDDS matrix. The resultant formulation matrices perform as immediate release products.

Table 10 summarizes the compositions evaluated in Example 10. The basic procedures to be employed for the preparation of these SEDDS combinations include:
(i) Transferring $\Delta^9$-THC into a clean beaker and heating the ingredients to 65-70° C.;

TABLE 10

| | Composition mg of ingredient per placebo formulation (% per caps) | | |
|---|---|---|---|
| | # 17 | # 18 | # 19 |
| Active Agent | 10.0 (3.85) | 10.0 (3.85) | 10.0 (3.85) |
| Oil Component (Oleic Acid) | 120.0 (46.15) | 120.0 (46.2) | 155.0 (59.62) |
| Surfactant Component (Cremophor EL) | 120.0 (46.15) | 95.0 (36.5) | 57.0 (21.92) |
| Surfactant Component (Labrafil M1944CS) | — | 25.0 (9.61) | 20.0 (7.69) |
| Vitamin E, FCC | 5.0 (1.925) | 5.0 (1.925) | 5.0 (1.925) |
| Ascorbyl Palmitate | 5.0 (1.925) | 5.0 (1.925) | 13.0 (5.0) |
| Total* | 260 (100) | 260 (100) | 260 (100) |

The variations in surfactant component do not alter the release profile pattern as with the original compositions. The dissolution process is nearly complete within 1 hour in 2% SLS media (paddle, 75 RPM). Furthermore, additional examples can substitute a multitude of different surfactant components. Finally, it was realized that during formulation preparation, processing temperatures can reach as high as 65-70° C. This does not adversely impact the chemical and physical characteristics of the $\Delta^9$-THC SEDDS matrices.

Example 11

Based on initial compositions (Table 1) as well as information from Example 10, additional $\Delta^9$-THC SEDDS compositions are tested with different surfactant components (i.e. Labrasol, Labrafil M1944CS). In addition, combinations of surfactants are tested in order to obtain a composite HLB value of approximately between 11-12 for optimal performance of a Type II SEDDS system. Finally, combinations of antioxidants are tested in order to optimize synergistic protection for the drug compound and SEDDS matrix. The resultant formulation matrices perform as immediate release products.

Table 11 summarizes the compositions evaluated in Example 11. The basic procedures to be employed for the preparation of these SEDDS combinations include:

(i) Transferring $\Delta^9$-THC into a clean beaker and heating the ingredients to 65-70° C.;

(ii) Slowly adding the oil component to the beaker;

(iii) Adding surfactant component to the clear mixture;

(iv) Stirring the contents well to form a homogeneous mixture and continuing to maintain the clear mixture at 65-70° C.;

(v) Adding the required quantity of Ascorbyl Palmitate into the above melt matrix slowly under stirring and continue heating at 65-70° C. until it dissolves/melts to form a homogeneous formulation matrix; and (vi) Filling the formulation matrix with the help of a pipette into a capsule size "1 (hypromellose or hard gelatin) as per the target weight and allowing to cool to room temperature to form a semi-solid matrix or liquid

TABLE 11

| | Composition mg of ingredient per placebo formulation (% per caps) | | |
|---|---|---|---|
| | # 20 | # 21 | # 22 |
| Active Agent | 10.0 (3.85) | 10.0 (3.85) | 10.0 (3.85) |
| Oil Component (Oleic Acid) | 120.0 (46.15) | 120.0 (46.2) | 155.0 (59.62) |
| Surfactant Component (Labrasol) | 120.0 (46.15) | 95.0 (36.5) | 57.0 (21.92) |
| Surfactant Component (Labrafil M1944CS) | — | 25.0 (9.61) | 20.0 (7.69) |

TABLE 11-continued

| | Composition mg of ingredient per placebo formulation (% per caps) | | |
|---|---|---|---|
| | # 20 | # 21 | # 22 |
| Vitamin E, FCC | 5.0 (1.925) | 5.0 (1.925) | 5.0 (1.925) |
| Ascorbyl Palmitate | 5.0 (1.925) | 5.0 (1.925) | 13.0 (5.0) |
| Total* | 260 (100) | 260 (100) | 260 (100) |

The variations in surfactant component do not alter the release profile pattern as with the original compositions. The dissolution process is nearly complete within 1 hour in 2% SLS media (paddle, 75 RPM). Furthermore, additional examples may be performed by substituting a multitude of different surfactant components. During formulation preparation, processing temperatures can reach as high as 65-70° C. This does not adversely influence the chemical and physical characteristics of the $\Delta^9$-THC SEDDS matrices.

Example 12

Based on initial compositions (Table 1) as well as information obtained from Example 9, additional $\Delta^9$-THC SEDDS compositions are tested to optimize dissolution parameters for semi-solid formulations with high ascorbyl palmitate content loading. Furthermore, the resultant formulation matrices perform as sustained release products.

Table 12 summarizes the compositions evaluated in Example 12. The basic procedures to be employed for the preparation of these SEDDS combinations include:

(i) Transferring $\Delta^9$-THC into a clean beaker and heating the ingredients to 65-70° C.;

(ii) Slowly adding the oil component to the beaker;

(iii) Adding surfactant component to the clear mixture;

(iv) Stirring the contents well to form a homogeneous mixture and continuing to maintain the clear mixture at 65-70° C.;

(v) Adding the required quantity of Ascorbyl Palmitate into the above melt matrix slowly under stirring and continuing heating at 65-70° C. until it dissolves/melts to form a homogeneous formulation matrix; and (vi) Filling the formulation matrix with the help of a pipette into a capsule size "1 (hypromellose or hard gelatin) as per the target weight and allow to cool to room temperature to form a semi-solid matrix or liquid

TABLE 12

| | Composition mg of ingredient per placebo formulation (% per caps) | | | |
|---|---|---|---|---|
| | # 23 | # 24 | # 25 | # 26 |
| Active Agent | 10.0 (3.85) | 10.0 (3.85) | 10.0 (3.85) | 10.0 (3.85) |
| Oil Component (Oleic Acid) | 109.5 (42.12) | 109.5 (42.12) | 150.0 (57.69) | 150.0 (57.69) |
| Surfactant Component (Cremophor EL) | 87.5 (33.65) | — | 55.0 (21.15) | — |
| Surfactant Component (Labrasol) | — | 87.5 (33.65) | — | 55.0 (21.15) |
| Surfactant Component (Labrafil M1944CS) | 22.0 (8.46) | 22.0 (8.46) | 20.0 (7.69) | 20.0 (7.69) |
| Vitamin E, FCC | 5.0 (1.925) | 5.0 (1.925) | 5.0 (1.925) | 5.0 (1.925) |
| Ascorbyl Palmitate | 26.0 (10.00) | 26.0 (10.00) | 20.0 (7.69) | 20.0 (7.69) |

Figure 3:
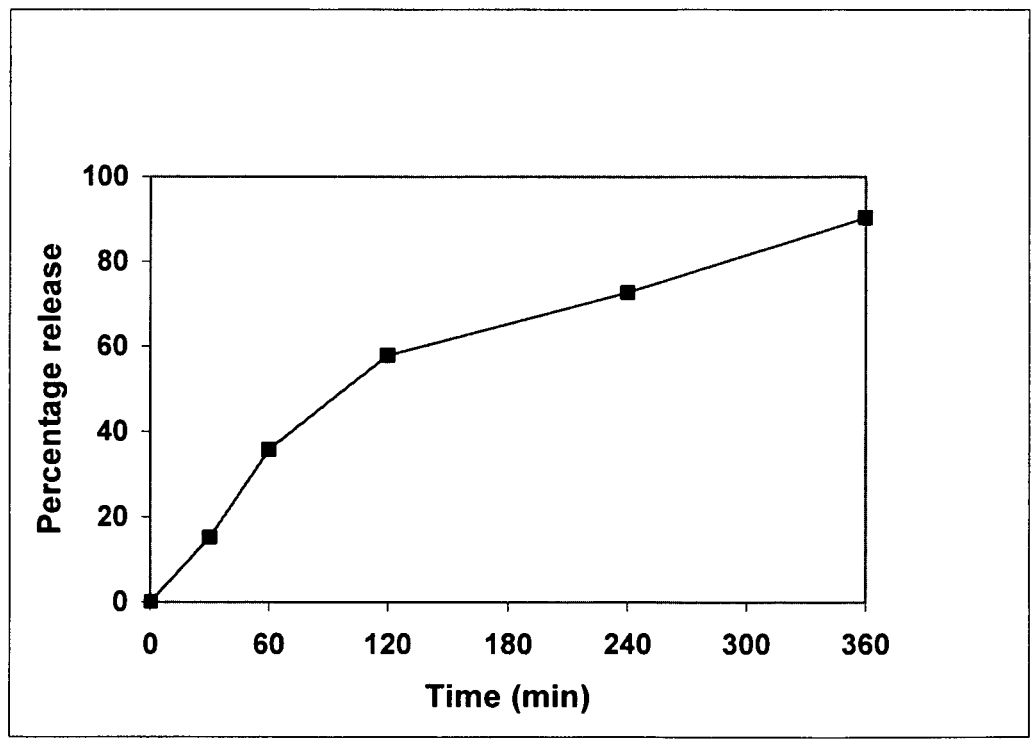
FIG. 3 is a graph showing the dissolution profile of a cannabinoid containing formulation of the present invention illustrating, in particular, the sustained drug release pattern over a four to six-hour period.

The use of high ascorbyl palmitate concentrations can result in sustained drug release pattern over a 4 to 6 hour period in 2% SLS media (paddle, 75 RPM), as illustrated in FIG. 3 (Dissolution Profiles for Formulation #25 in Hard Gelatin and Hypromellose Capsule Shells). The prolonged drug release rates are attributed to the formation of a semi-solid matrix. It is found that the semi-solid matrix induced by the ascorbyl palmitate serves as a stabilizing mechanism for a compound such as $\Delta^9$-THC, which illustrates a high oxidation potential. It is realized during formulation preparation that processing temperatures can reach as high as 65-70° C. This does not adversely impact the chemical and physical characteristics of the $\Delta^9$-THC SEDDS matrices.

Example 13

Based on initial compositions (Table 1) as well as information obtained from Examples 6, 10, & 11, additional $\Delta^9$-THC SEDDS compositions are evaluated to determine the effect of additional oily components (i.e. Peppermint Oil) on dissolution properties in 2% SLS media (see Example 2). The resultant formulation matrices perform as immediate release products.

Table 13 summarizes the compositions evaluated in Example 13. The basic procedures to be employed for the preparation of these SEDDS combinations include:
(i) Transferring $\Delta^9$-THC into a clean beaker and heating the ingredients to 65-70° C.;
(ii) Slowly adding the oil component to the beaker;
(iii) Adding surfactant component to the clear mixture;
(iv) Stirring the contents well to form a homogeneous mixture and continuing to maintain the clear mixture at 65-70° C.;
(v) Adding the required quantity of Ascorbyl Palmitate into the above melt matrix slowly under stirring and continue heating at 65-70° C. until it dissolves/melts to form a homogeneous formulation matrix; and
(vi) Filling the formulation matrix with the help of a pipette into a capsule size "1 as per the target weight and allow to cool to room temperature to form a semi-solid matrix or liquid.

different oil components. Finally, it is realized during formulation preparation, that processing temperatures can reach as high as 65-70° C. This does not adversely influence the chemical and physical characteristics of the $\Delta^9$-THC SEDDS matrices.

Example 14

Based on the information provided in Example 10, Formulation #18 is evaluated under ICH stability testing conditions (i.e. 2-8° C., 25° C./60% RH, & 40° C./75% RH). After storing hard gelatin filled capsules and bulk formulation solutions from Formulation #18 for three months, parameters are evaluated as described in Table 14.

The combination of Vitamin E, FCC (DL-α-Tocopherol) and Ascorbyl Palmitate provides synergistic stabilization effects for both the drug compound as well as the SEDDS matrix. Table 14 below provides the evaluation results, which show the efficacy of antioxidants in maintaining the stability of the drug compound as well as the integrity of the capsule shell.

TABLE 14

| Conditions | Time (Months) | Capsule Description | Assay | Related and Degradation Substances | |
|---|---|---|---|---|---|
| | | | | CBN | Delta-8 THC |
| N/A | Initial | No Deformity | 99.3% | 2.3% | NA |
| 2°-8° C. | 1 | No Deformity | 97.1% | 1.9% | 1.0% |
| | 2 | No Deformity | 98.6% | 1.7% | 1.0% |
| | 3 | No Deformity | 97.7% | 2.2% | 1.1% |
| 25° C./60% RH | 1 | No Deformity | 99.0% | 2.8% | 1.5% |
| | 2 | No Deformity | 99.0% | 1.8% | 0.9% |
| | 3 | No Deformity | 98.7% | 2.2% | 0.9% |
| 40° C./75% RH | 1 | No Deformity | 95.3% | 2.4% | 1.5% |
| | 2 | No Deformity | 96.5% | 1.9% | 0.8% |
| | 3 | No Deformity | 96.2% | 2.2% | 1.1% |

TABLE 13

| | Composition mg of ingredient per formulation (% per caps) | | | |
|---|---|---|---|---|
| | # 27 | # 28 | # 29 | # 30 |
| Active Agent | 10 (3.85) | 10 (3.85) | 10 (3.85) | 10 (3.85) |
| Oil Component (Oleic Acid) | 95.0 (36.54) | 120.0 (46.15) | 95.0 (36.54) | 120.0 (46.15) |
| Oil Component (Peppermint Oil, USP-NF) | 25.0 (9.615) | 25.0 (9.615) | 25.0 (9.615) | 25.0 (9.615) |
| Surfactant Component (Cremophor EL) | 95.0 (36.54) | 75.0 (28.85) | — | — |
| Surfactant Component (Labrasol) | — | — | 95.0 (36.54) | 75.0 (28.85) |
| Surfactant Component (Labrafil M1944CS) | 25.0 (9.615) | 20.0 (7.692) | 25.0 (9.615) | 20.0 (7.692) |
| Vitamin E, FCC | 5.0 (1.925) | 5.0 (1.925) | 5.0 (1.925) | 5.0 (1.925) |
| Ascorbyl Palmitate | 5.0 (1.925) | 5.0 (1.925) | 5.0 (1.925) | 5.0 (1.925) |
| Total* | 260 (100) | 260 (100) | 260 (100) | 260 (100) |

The additional oil component does not alter the release profile pattern as with the original compositions (Table 1). The dissolution process is nearly complete within 1 hour in 2% SLS media (paddle, 75 RPM). Furthermore, additional examples may be evaluated by substituting a multitude of Example 15

Additional $\Delta^9$-THC SEDDS compositions are evaluated to determine the effect of additional oily components (e.g., Maisine 35-1) as well as co-solvents (e.g., ethanol) on dissolution properties in 2% SLS media (see Example 2). The resultant formulation matrices perform as immediate release products.

Table 15 summarizes the compositions evaluated in Example 15. The basic procedures to be employed for the preparation of these Type III SEDDS combinations include:
(i) Transferring $\Delta^9$-THC into a clean beaker and heating the ingredients to 65-70° C.;
(ii) Slowly adding the oil component (s) to the beaker (Maisine 35-1 is heated to 50° C. before adding to the beaker);
(iii) Adding surfactant component to the clear mixture;
(iv) Stirring the contents well to form a homogeneous mixture and continuing to maintain the clear mixture at 65-70° C.;
(v) Adding the required quantity of Ascorbyl Palmitate into the above melt matrix slowly under stirring and continue heating at 65-70° C. until it dissolves/melts to form a homogeneous formulation matrix;
(vi) Cooling down the beaker contents and adding Ethanol; and
(vii) Filling the formulation matrix with the help of a pipette into the appropriate capsule size as per the target weight and allow to cool to room temperature to form a semi-solid matrix or liquid.

TABLE 15

| Ingredient | Formulation # 31 mg (% of Formulation); | Formulation # 32 mg (% of Formulation); |
|---|---|---|
| Delta-9-Tetrahydrocannabinol | 10 mg (1.25%) | 10 mg (1.25%) |
| Soybean Oil, USP-NF | 225 mg (28.125%) | 140.625 mg (17.578%) |
| Maisine 35-1 (Glyceryl Monolinoleate) | 225 mg (28.125%) | 140.625 mg (17.578%) |
| Peppermint Oil, USP-NF | 20 mg (2.5%) | 20 mg (2.5%) |
| Cremophor RH 40 | 225 mg (28.125%) | 412.5 mg (51.563%) |
| Vitamin E, FCC | 10 mg (1.25%) | 10 mg (1.25%) |
| Ascorbyl Palmitate | 10 mg (1.25%) | 10 mg (1.25%) |
| Ethanol (USP, 200 Proof) | 75 mg (9.375%) | 56.25 mg (7.03%) |
| Total Capsule Fill Weight | 800 mg | 800 mg |

Example 16

Based on information obtained from Example 15, additional Type III SEDDS compositions are evaluated to determine the effect of adding standardized marijuana extract (i.e., *Cannabis sativa* extract) on dissolution properties in 2% SLS media (see Example 2). The resultant formulation matrices also perform as immediate release products.

Table 16 summarizes the compositions evaluated in Example 16. The basic procedures to be employed for the preparation of these Type III SEDDS combinations include:
(i) Transferring the Standardized Marijuana Extract (dissolved in 1 mL ethanol) into a clean beaker and gently heating the ingredients to 35-40° C.;
(ii) Slowly adding the oil component (s) to the beaker (Maisine 35-1 is heated to 50° C. before adding to the beaker);
(iii) Adding surfactant component to the clear mixture;
(iv) Stirring the contents well to form a homogeneous mixture and continuing to maintain the clear mixture at 65-70° C.;
(v) Adding the required quantity of Ascorbyl Palmitate into the above melt matrix slowly under stirring and continue heating at 65-70° C. until it dissolves/melts to form a homogeneous formulation matrix;
(vi) Cooling down the beaker contents and adding Ethanol; and
(vii) Filling the formulation matrix with the help of a pipette into the appropriate capsule size as per the target weight and allow to cool to room temperature to form a semi-solid matrix or liquid.

TABLE 6

| Ingredient | Formulation # 33 mg (% of Formulation); | Formulation # 34 mg (% of Formulation); |
|---|---|---|
| Standardized Marijuana Extract (Dissolved in 1 mL Ethanol)* | 10 mg (1.25%) | 10 mg (1.25%) |
| Soybean Oil, USP-NF | 225 mg (28.125%) | 140.625 mg (17.578%) |

TABLE 6-continued

| Ingredient | Formulation # 33 mg (% of Formulation); | Formulation # 34 mg (% of Formulation); |
|---|---|---|
| Maisine 35-1 (Glyceryl Monolinoleate) | 225 mg (28.125%) | 140.625 mg (17.578%) |
| Peppermint Oil, USP-NF | 20 mg (2.5%) | 20 mg (2.5%) |
| Cremophor RH 40 | 225 mg (28.125%) | 412.5 mg (51.563%) |
| Vitamin E, FCC | 10 mg (1.25%) | 10 mg (1.25%) |
| Ascorbyl Palmitate | 10 mg (1.25%) | 10 mg (1.25%) |
| Ethanol (USP, 200 Proof) | 75 mg (9.375%) | 56.25 mg (7.03%) |
| Total Capsule Fill Weight | 800 mg | 800 mg |

*Contains cannabinoid class phytochemicals including cannabigerol (CBG), cannabichromeme (CBC), cannabidiol (CBD), delta-9-tetrahydrocannabinol, delta-8-tetrahydrocannabinol, cannabicyclol (CBL), cannabielsoin (CBE), cannabinol (CBN), cannabinodiol (CBDL), and cannabitriol (CBTL), etc.

Although specific embodiments of the present invention have been disclosed herein, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. An oral dosage form of cannabinoids in a self-emulsifying system operable to avoid hepatic first pass metabolism via targeted chylomicron/lipoprotein delivery, thereby promoting lymphatic transport, said oral dosage form comprising:
(a) about 1-60 wt % of a pharmacologically active form of cannabinoids selected from the group consisting of tetrahydrocannabinol, $\Delta^9$-tetrahydrocannabinol (THC), $\Delta^8$-tetrahydrocannabinol, $\Delta^8$-tetrahydrocannabinol-DMH, $\Delta^9$-tetrahydrocannabinol propyl analogue (THCV), 11-hydroxy-tetrahydrocannabinol, 11-nor-9-carboxy-tetrahydrocannabinol, 5'-azido-$\Delta^8$-tetrahydrocannabinol, AMG-1, AMG-3, AM411, AM708, AM836, AM855, AM919, AM926, AM938, cannabidiol (CBD), cannabidiol propyl analogue (CBDV), cannabinol (CBN), cannabichromene, cannabichromene propyl analogue, cannabigerol, CP 47497, CP 55940, CP 55244, CP 50556, CT-3 (ajulemic acid), dimethylheptyl HHC, HU-210, HU-211, HU-308, WIN 55212-2, desacetyl-L-nantradol, dexanabinol, JWH-051, levonantradol, L-759633, nabilone, 0-1184, and mixtures thereof;
(b) about 15-35 wt % of one or more triglycerides formed from long chain fatty acids having from $C_{13}$ to $C_{24}$ carbon atoms, selected from the group consisting of borage oil, coconut oil, cottonseed oil, soybean oil, safflower oil, sunflower oil, castor oil, corn oil, olive oil, palm oil, peanut oil, poppy seed oil, canola oil, hydrogenated soybean oil, hydrogenated vegetable oils, triolein, trilinolein, and trilinolenin;
(c) about 15-35 wt % of one or more mixed glycerides formed from fatty acids having from $C_{13}$ to $C_{24}$ carbon atoms, said one or more mixed glycerides being selected from the group consisting of glyceryl behenate, glyceryl distearate, glyceryl isostearate, glyceryl laurate, glyceryl monooleate, glyceryl monolinoleate, glyceryl palmitate, glyceryl palmitostearate, glyceryl ricinoleate, glyceryl stearate, polyglyceryl 10-oleate, polyglyceryl 3-oleate, polyglyceryl 4-oleate, and polyglyceryl 10-tetralinoleate;
(d) about 10-60 wt % of a surfactant which promotes self-emulsification, said surfactant being selected from the group consisting of almond oil PEG-6 esters, almond oil PEG-60 esters, apricot kernel oil PEG-6 esters, caprylic/capric triglycerides PEG-4 esters, caprylic/capric triglycerides PEG-4 complex, caprylic/capric glycerides PEG-6 esters, caprylic/capric glycerides PEG-8 esters, castor oil PEG-50 esters, hydrogenated castor oil PEG-5 esters, hydrogenated castor oil PEG-7 esters, 9 hydrogenated castor oil PEG-9 esters, corn oil PEG-6 esters, corn oil PEG-8 esters, corn glycerides PEG-60 esters, olive oil PEG-6 esters, hydrogenated palm/palm kernel oil PEG-6 esters, hydrogenated palm/palm kernel oil PEG-6 esters with palm kernel oil and PEG-6 and palm oil, palm kernel oil PEG-40 esters, peanut oil PEG-6 esters, glycerol esters of saturated C8-C18 fatty acids, glyceryl esters of saturated C12-C18 fatty acids, glyceryl laurate/PEG-32 laurate, glyceryl laurate glyceryl/PEG 20 laurate, glyceryl laurate glyceryl/PEG 32 laurate, glyceryl laurate, glyceryl/PEG 40 laurate, glyceryl oleate/PEG-20 glyceryl, glyceryl oleate PEG-30 oleate, glyceryl palmitostearate/PEG-32 palmitostearate, glyceryl stearate/PEG stearate, glyceryl stearate/PEG-32 stearate, saturated polyglycolized glycerides, triisostearin PEG-6 esters, triolein PEG-6 esters, trioleate PEG-25 esters, polyoxyl 35 castor oil, polyoxyl 40 hydrogenated castor oil, polyoxyl 60 hydrogenated castor oil, PEG-8 caproate, PEG-8 caprylate, PEG-8 caprate PEG-8 laurate, PEG-8 oleate, PEG-8 stearate, PEG-9 caproate, PEG-9 caprylate, PEG-9 caprate PEG-9 laurate, PEG-9 oleate, PEG-9 stearate, PEG-10 caproate, PEG-10 caprylate, PEG-10 caprate PEG-10 laurate, PEG-10 oleate, PEG-10 stearate, PEG-10 laurate, PEG-12 oleate, PEG-15 oleate, PEG-20 laurate, PEG-20 oleate, caprylyic/capric glycerides, caprylate/caprate diglycerides, glyceryl monooleate, glyceryl ricinoleate, glyceryl laurate, glyceryl dilaurate, glyceryl dioleate, glyceryl mono/dioleate, glyceryl caprylate/caprate, medium chain C8/C10 mono- and diglycerides, mono- and diacetylated monoglycerides, polyglyceryl oleate, polyglyceryl-2 dioleate, polyglyceryl-10 trioleate, polyglyceryl-10 laurate, polyglyceryl-10 oleate, polyglyceryl-10 mono dioleate, propylene glycol caprylate/caprate, propylene glycol dicaprylate/dicaprate, propylene glycol monolaurate, propylene glycol ricinoleate, propylene glycol monooleate, propylene glycol dicaprylate/dicaprate, propylene glycol dioctanoate, PEG-20 sorbitan monolaurate, PEG-20 sorbitan monopalmitate, PEG-20 sorbitan monostearate, PEG-20 sorbitan monooleate, poloxamer 108, poloxamer 124, poloxamer 182, poloxamer 183, poloxamer 188, poloxamer 212, poloxamer 217, poloxamer 238, poloxamer 288, poloxamer 331, poloxamer 338, poloxamer 335, poloxamer 407, sorbitan monolaurate, sorbitan monopalmitate, sorbitan monoleate, sorbitan monostearate, sorbitan tristearate, d-α-tocopheryl polyethylene glycol 1000 succinate, polysorbate 20, polysorbate, polyethyleneglycol 660 12-hydroxystearate, and mixtures thereof; and (e) free fatty acids having from $C_{13}$ to $C_{24}$ carbon atoms wherein one or more free of the fatty acids are selected from the group consisting of, behenic acid, lauric acid, linoleic acid, linolenic acid, myristic acid, palmitic acid, palmitoleic acid, palmitostearic acid, ricinoleic acid, soy fatty acids, oleic acid, and mixtures thereof.

2. The oral dosage form of cannabinoids of claim 1, wherein the one or more triglycerides and one or more mixed glycerides are present in a weight ratio of about 15:85 to 85:15.

3. The oral dosage form of cannabinoids of claim 1, wherein the one or more triglycerides and one or more mixed glycerides are present in a weight ratio of about 30:70 to 70:30.

4. The oral dosage form of cannabinoids of claim 1, wherein the one or more triglycerides and one or more mixed glycerides are present in a weight ratio of about 45:55 to 55:45.

5. The oral dosage form of cannabinoids in a self emulsifying system of claim 1, further comprising cosolvents, solubilizing agents and antioxidants selected from the group consisting of ethanol, polyethylene glycol 300, polyethylene glycol 400, propylene glycol, propylene carbonate, N-methyl-2-pyrrolidones, dimethylacetamide, dimethyl sulfoxide, hydroxypropyl-β-cyclodextrins, sulfobutylether-β-cyclodextrin, α-cyclodextrin, HSPC phospholipid, DSPG phospholipid, DMPC phospholipid, DMPG phospholipid, ascorbyl palmitate, butylated hydroxy anisole, butylated hydroxy toluene, propyl gallate, α-tocopherol, and γ-tocopherol, and mixtures thereof.

6. The oral dosage form of cannabinoid of claim 1, further comprising:
(f) about 1-80 wt % of solubilizing co-solvents; and
(g) about 0.01-15 wt % of antioxidants.

7. The oral dosage form of cannabinoid of claim 1, further comprising:
(f) about 5-50 wt % of solubilizing co-solvent; and
(g) about 0.01-12.5 wt % of antioxidant.

8. The oral dosage form of cannabinoids of claim 1, further comprising about 2.5-15 wt % of a semi-solid inducer.

9. The oral dosage form of cannabinoids of claim 8, wherein the semi-solid inducer is ascorbyl palmitate.

10. A method of avoiding and/or suppressing hepatic first pass metabolism of an orally administered cannabinoid after administration to the mammalian intestinal tract by targeted chylomicron/lipoprotein delivery in order to promote lymphatic transport, said method comprising orally administering said cannabinoid in an oral dosage form according to the composition of claim 1.

11. An oral dosage form of cannabinoids in a self-emulsifying system operable to avoid hepatic first pass metabolism via targeted chylomicron/lipoprotein delivery, thereby promoting lymphatic transport, said oral dosage form comprising:

(a) about 1-60 wt % of a pharmacologically active form of cannabinoids selected from the group consisting of tetrahydrocannabinol, $\Delta^9$-tetrahydrocannabinol (THC), $\Delta^8$-tetrahydrocannabinol, $\Delta^8$-tetrahydrocannabinol-DMH, $\Delta^9$-tetrahydrocannabinol propyl analogue (THCV), 11-hydroxy-tetrahydrocannabinol, 11-nor-9-carboxy-tetrahydrocannabinol, 5'-azido-$\Delta^8$-tetrahydrocannabinol, AMG-1, AMG-3, AM411, AM708, AM836, AM855, AM919, AM926, AM938, cannabidiol (CBD), cannabidiol propyl analogue (CBDV), cannabinol (CBN), cannabichromene, cannabichromene propyl analogue, cannabigerol, CP 47497, CP 55940, CP 55244, CP 50556, CT-3 (ajulemic acid), dimethylheptyl HHC, HU-210, HU-211, HU-308, WIN 55212-2, desacetyl-L-nantradol, dexanabinol, JWH-051, levonantradol, L-759633, nabilone, 0-1184, and mixtures thereof;

(b) about 15-35 wt % of one or more triglycerides formed from long chain fatty acids having from $C_{13}$ to $C_{24}$ carbon atoms;

(c) about 15-35 wt % of one or more mixed glycerides formed from fatty acids having from $C_{13}$ to $C_{24}$ carbon atoms; and (d) about 10-60 wt % of a surfactant which promotes self-emulsification, said surfactant selected from the group consisting of polyglycolized glycerides, polyoxyethylene glycerides, polyethylene glycol-fatty acid esters, polyethylene glycol glycerol fatty acid esters, transesterification products of oils and alcohols, polyglycerized fatty acids, glycerol fatty acid esters, polyglycerol fatty acid esters, propylene glycol fatty acid esters, mono and diglycerides, polyethylene glycol sorbitan fatty acid esters, polyoxyethylene-polyoxypropylene block copolymers, sorbitan fatty acid esters, d-α-tocopheryl polyethylene glycol 1000 succinate, polyoxyethyleneglycol 660 12-hydroxystearate, polysorbates, and mixtures thereof.

* * * * *